(12) United States Patent
Strecker

(10) Patent No.: US 7,212,701 B2
(45) Date of Patent: May 1, 2007

(54) METHODS FOR MEASURING OPTICAL ABSORBANCE OF A SAMPLE MEDIUM

(75) Inventor: Brian N. Strecker, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 0 days.

(21) Appl. No.: 11/473,887

(22) Filed: Jun. 23, 2006

(65) Prior Publication Data

US 2006/0239606 A1    Oct. 26, 2006

Related U.S. Application Data

(62) Division of application No. 11/077,834, filed on Mar. 11, 2005, now Pat. No. 7,177,492.

(60) Provisional application No. 60/552,158, filed on Mar. 11, 2004.

(51) Int. Cl.
*G02B 6/12* (2006.01)
*G01B 9/02* (2006.01)
(52) U.S. Cl. .................. 385/14; 385/30; 356/480
(58) Field of Classification Search ............ 385/14–15, 385/27, 30, 39; 356/436
See application file for complete search history.

(56) References Cited

U.S. PATENT DOCUMENTS

| | | |
|---|---|---|
| 4,963,498 A | 10/1990 | Hillman et al. |
| 6,125,220 A | 9/2000 | Copner et al. |
| 6,281,977 B1 | 8/2001 | Paiam et al. |
| 6,490,039 B2 * | 12/2002 | Maleki et al. ............... 356/436 |
| 7,095,010 B2 * | 8/2006 | Scherer et al. .......... 250/227.11 |

OTHER PUBLICATIONS

J. C. Knight, G. Cheung, F. Jacques, and T. A. Birks, "Phase-matched excitation of whispering-gallery-mode resonances by a fiber taper", Optics Letters, Aug. 1, 1997, pp. 1129-1131, vol. 22, No. 15, Optoelectronics Group, School of Physics, University of Bath, Bath BA2 7AY, UK.

M. Selim Unlu, "Resonant-cavity-enhanced devices improve efficiency", Optoelectronics World magazine, Mar. 1998, pp. 15-20, vol. 34, No. 3, Optoelectronics World (online), PennWell, 1421 South Sheridan, Tulsa, Oklahoma, USA.

Lutfollah Maleki, Vladimir Iltchenko and Xiaotian Steve Yao, "Highly Oblate Microspheroid as an Optical Resonator", NASA Tech Brief, from JPL New Technology Report NPO-20951, Apr. 1, 2001, 7 pages, vol. 25, No. 4, Jet Propulsion Laboratory California Institute of Technology, Pasadena, California, USA.

(Continued)

*Primary Examiner*—Quyen Leung
(74) *Attorney, Agent, or Firm*—Dunlap, Codding & Rogers, P.C.

(57) ABSTRACT

A method for measuring the optical absorbance of a sample medium with a microfluidic chip that includes a substrate defining a microfluidic channel, a microresonator positioned within the microfluidic channel, and at least one waveguide or coupling surface evanescently coupled to the microresonator such that only supported Whispering Gallery Mode (WGM) resonance frequencies are transmitted from the waveguide or coupling surface into the microresonator. A sample medium is disposed into the microfluidic channel to substantially envelop the microresonator and a reader is provided to measure at least a portion of the WGM frequencies transmitted out of the microresonator.

29 Claims, 13 Drawing Sheets

OTHER PUBLICATIONS

Vladimir Iltchenko and Lute Maleki, "Microshpere and Microcavity Optical-Absorption Sensors", NASA Tech Brief, from JPL New Technology Report NPO-21061, Apr. 1, 2001, 9 pages, vol. 25, No. 4, Jet Propulsion Laboratory California Institute of Technology, Pasadena, California, USA.

M. L. M. Balistreri et al., "Experimental analysis of the whispering-gallery modes in a cylindrical optical microcavity", J. Opt. Soc. Am. B, Apr. 2001, 7 pages, vol. 18, No. 4, Optical Society of America, USA.

Vladimir Iltchenko and Lute Maleki, "Simple Fiber-Optic Coupling for Microsphere Resonators", NASA Tech Brief, from JPL New Technology Report NPO-20619, May 2001, pp. 465-471, NPO-20619, Jet Propulsion Laboratory California Institute of Technology, Pasadena, California, USA.

H. Ishikawa, H. Tamaru, and K. Miyano, "Optical coupling between a microresonator and an adjacent dielectric structure: effects of resonator size", J. Opt. Soc. Am. B, Jun. 2001, pp. 762-769, vol. 18, No. 6, Optical Society of America, USA.

Thomas Lee S., Nibu A. George, P. Sureshkumar, P. Radhakrishnan, C. P. G. Vallabhan and V. P. N. Nampoori, "Chemical sensing with microbent optical fiber", Optics Letters, Oct. 15, 2001, pp. 1541-1543, vol. 26, No. 20, Optical Society of America, USA.

* cited by examiner

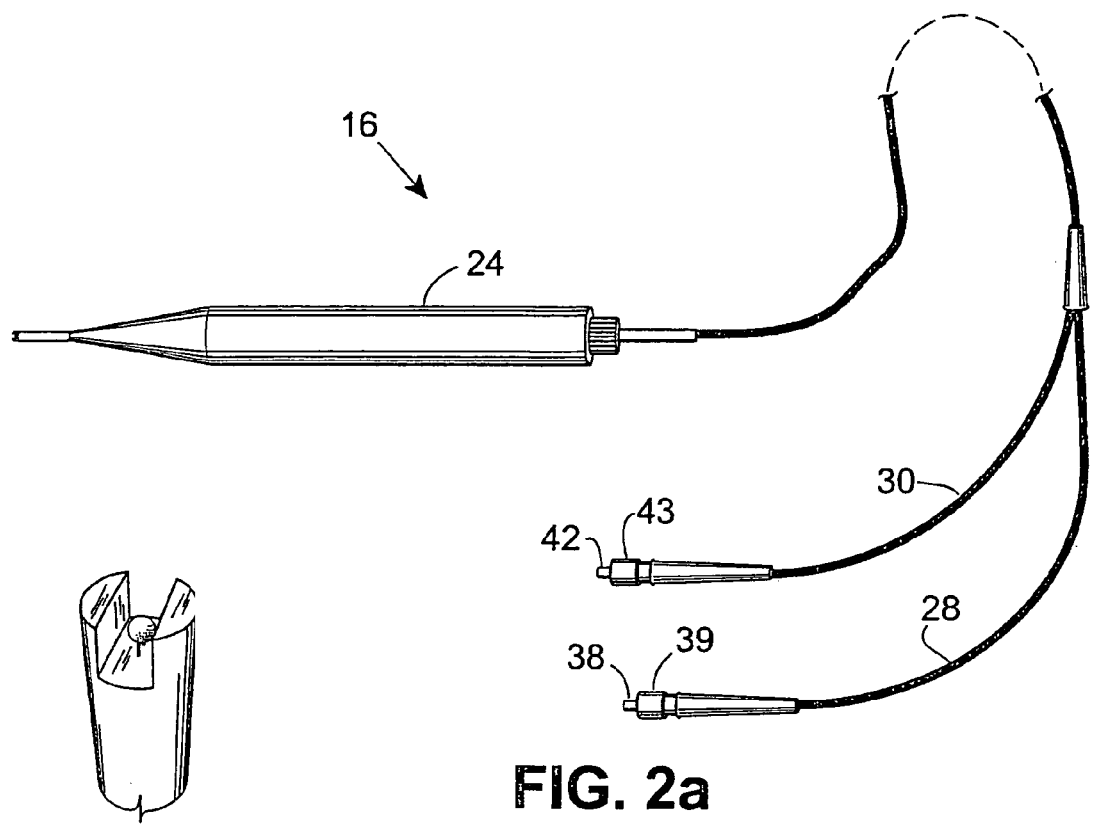
FIG. 2a
FIG. 2b
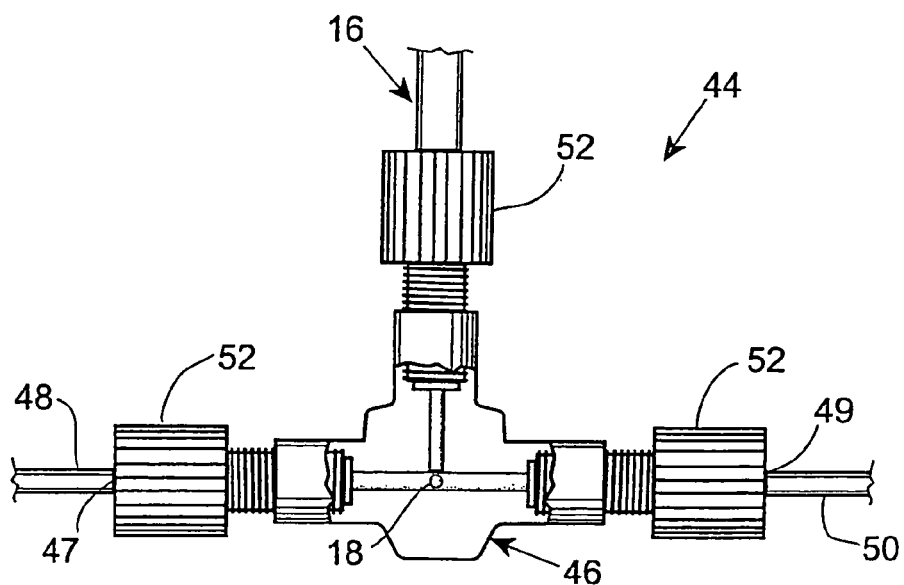
FIG. 3

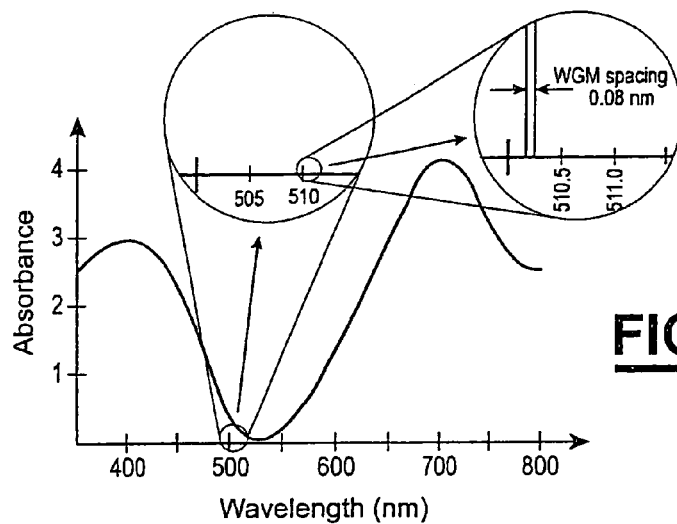
FIG. 10
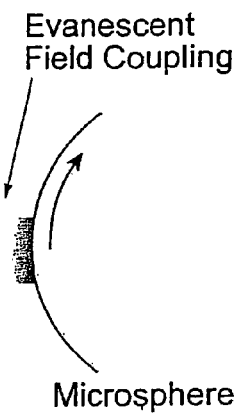
FIG. 11
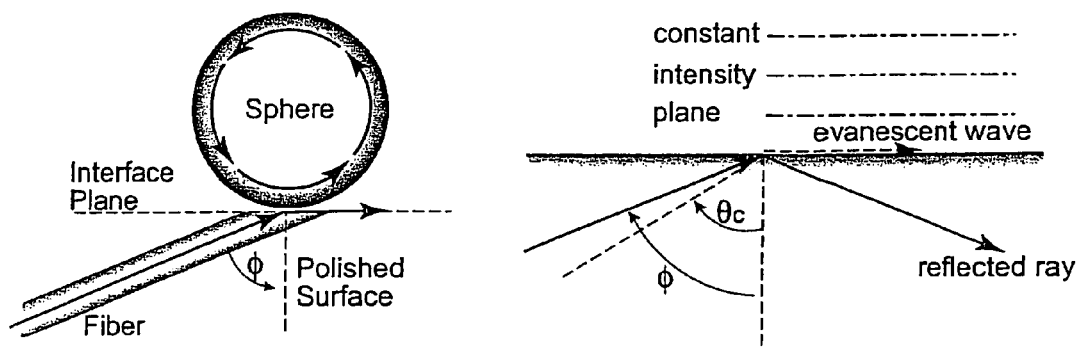
FIG. 12a      FIG. 12b

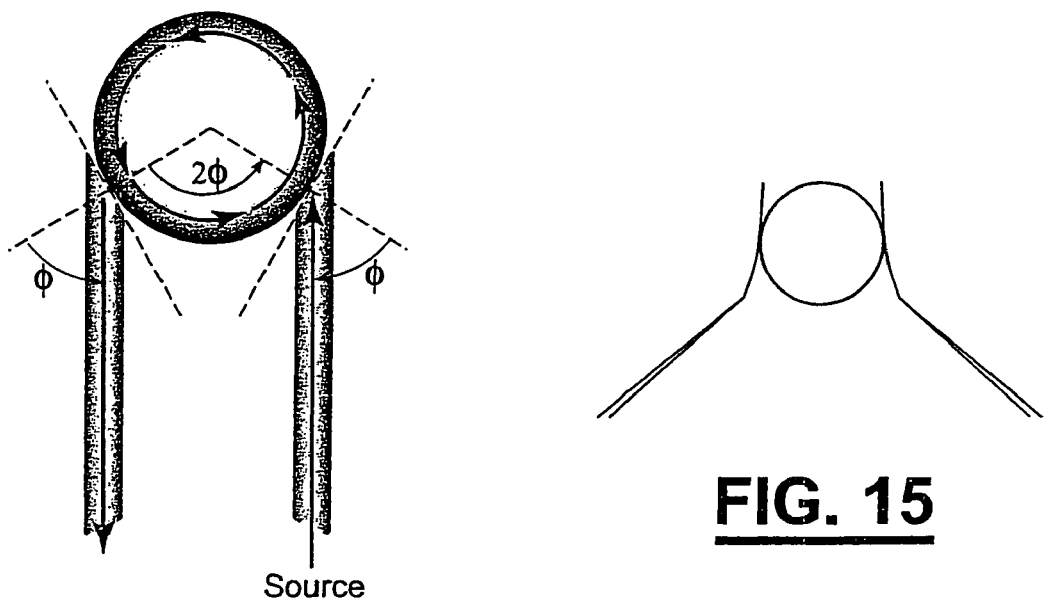
Source
FIG. 13
FIG. 15
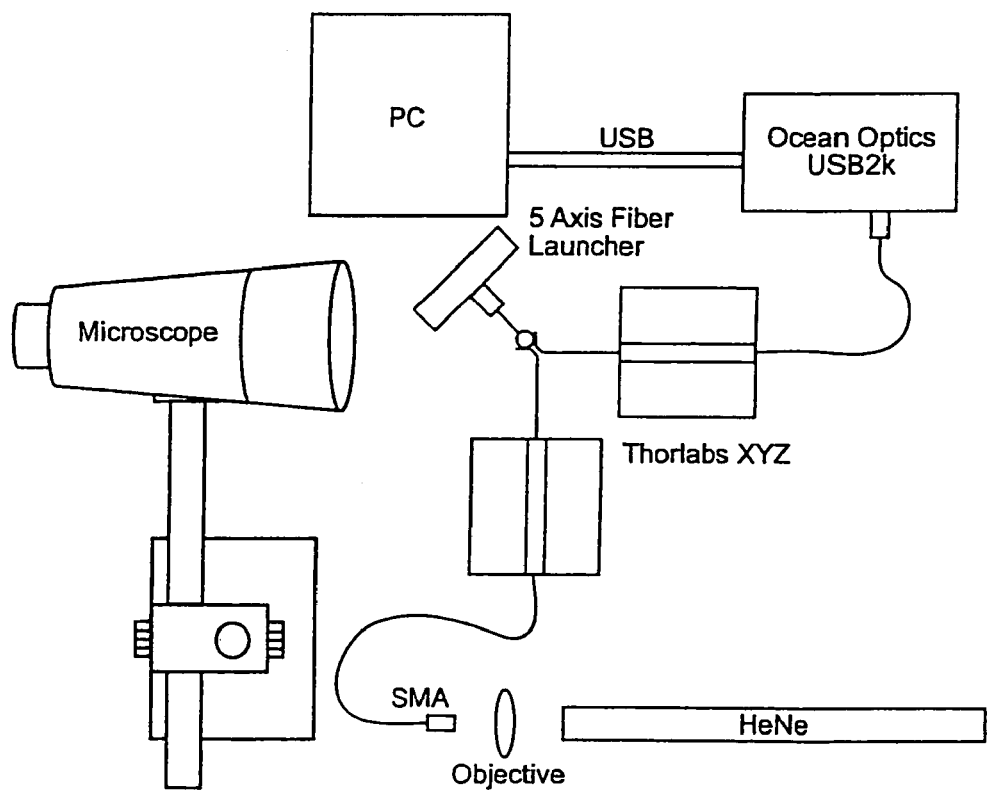
FIG. 14

Tapered fibers and the microsphere fiber are held Thorlabs fiber chucks

METHODS FOR MEASURING OPTICAL ABSORBANCE OF A SAMPLE MEDIUM

CROSS REFERENCE TO RELATED APPLICATIONS

This application is a divisional of U.S. Ser. No. 11/077,834 filed Mar. 11, 2005, now U.S. Pat. No. 7,177,492 which claims priority under 35 U.S.C. 119 to the provisional application Ser. No. 60/552,158, filed Mar. 11, 2004, entitled "SYSTEM FOR COLORIMETRIC TESTING OF FLUIDIC SAMPLES", which is hereby expressly incorporated herein by reference in its entirety.

FIELD OF THE INVENTION

DESCRIPTION OF THE PRIOR ART

Traditional systems for colorimetric testing generally provide a fixed length, single pass, optical path through a sample of liquid medium. Such traditional systems typically utilize a capillary micro-cuvette to contain the sample of liquid medium. In these traditional systems the sample of liquid medium is drawn into the capillary micro-cuvette to form a water core waveguide and, in operation, light from a light source propagates inside the water core waveguide before being received by a reader. One of the principal limitations of such traditional systems is the inconvenience of introducing and removing the sample of liquid medium from the system and the system's inability to conveniently support continuous flow monitoring.

Reducing the required volume of the sample of liquid medium needed to perform colorimetric testing reduces the cost of performing the colorimetric testing. Sample volume reduction in traditional systems is currently obtained by enhancing the path length to volume ratio by dimensional extension along the optical path and dimensional reduction perpendicular to the optical path. An improved way of enhancing the path length to sample volume ratio would lead to, among other things, reduced cost of sample analysis.

Therefore, there exists a need in the field of colorimetric testing for a system which would provide for convenient sample volume introduction and removal, an ability to support continuous flow monitoring and improved sample volume to path length ratios. It is to such a system that the present invention is directed.

BRIEF DESCRIPTION OF THE DRAWINGS

FIG. 2A is a perspective view of a probe for colorimetric testing.

FIG. 2B is a detailed view of the probe tip.

FIG. 3 is a side elevational view of an inline sample cell.

FIG. 10 shows the spacing of Whispering Gallery Modes in a 0.75 mm quartz spheroid of optically transparent material relative to a typical visible absorbance spectrum.

FIG. 11 shows the evanescent field coupling between a prism and a spheroid of optically transparent material.

FIGS. 12A and 12B depict the geometry of an angle polished fiber coupling and total internal reflection and evanescent wave.

FIG. 13 shows a first optical fiber having an angle polished first end in communication with a spheroid of optically transparent material and a second optical fiber having an angle polished first end in communication with the spheroid of optically transparent material.

FIG. 14 shows the arrangement of a fiber coupled 632 nm absorption experiment.

FIG. 15 shows the arrangement of the spheroid of optically transparent material and the tapered first ends of the first and second optical fibers.

DESCRIPTION OF THE PREFERRED EMBODIMENTS

Figure 1:
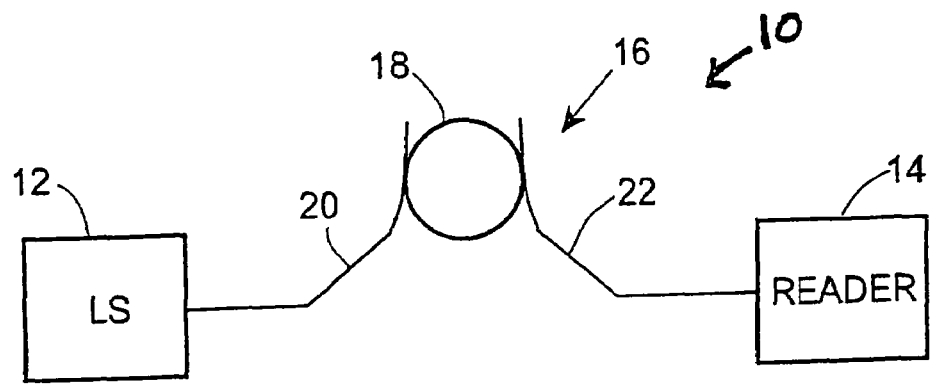
FIG. 1 is a schematic view of a system for colorimetric testing.

Referring now to FIG. 1 shown therein is a system 10 for the colorimetric testing of a sample constructed in accordance with the present invention. The system 10 includes a light source 12, a reader 14 and a probe 16. The probe 16 includes a resonator 18, a first coupler 20 and a second coupler 22. The probe 16 also can be provided with a handle 24 (FIG. 2A) for facilitating enclosure of and handling of at least a portion of the resonator 18, the first coupler 20 and the second coupler 22.

The light source 12 for the system 10 can be, for instance, a broad line width laser or an incoherent light source. For general purpose colorimetric testing, light sources 12 that can be utilized and are readily available commercially include, but are not limited to, tungsten quartz halogen bulbs. For colorimetric testing where a single spectral band provides sufficient information, the light source 12 can be a light emitting diode.

The reader 14 can be any reader capable of performing colorimetric testing, such as a spectrometer or an Si detector. A spectrometer which can be employed as the reader 14 is an Ocean Optics USB 2000, commercially available from Ocean Optics Inc., Dunedin, Fla.

The first and second couplers 20 and 22 are devices capable of transmitting light such as, optical fibers, planar waveguides, prisms or gratings capable of simultaneously directing a multitude of optical resonances. The first coupler 20, and the second coupler 22 of the probe 16 are coupled to the resonator 18. The first coupler 20 receives and couples at least a portion of the light from the light source 12 and directs the light coupled from the light source 12 into the resonator 18. The second coupler 22 of the probe 16 receives and couples at least a portion of the light coupled into the resonator 18 from the first coupler 20 and directs the light coupled from the resonator 18 to the reader 14. The portion of the light coupled from the resonator 18 and directed to the reader 14 is then analyzed by the reader 14.

The resonator 18 is constructed of optically transparent material shaped so as to constrain light to a repeating path and simultaneously support a multitude of optical resonances. For example, the resonator 18 can be a disc, torus, ring, cylinder, bloated cylinder or spheroid of optically transparent material capable of supporting a multitude of optical resonances. The resonator 18 can be constructed from silica, glass, quartz, gallium, silicon, or combinations and derivations thereof.

Light coupled into the resonator 18 is constrained to bands of frequencies known as Whispering Gallery Modes (WGM). Frequencies of light outside of the WGM's will not couple into the resonator 18. For use with broadband illumination, it is desirable to employ resonators supporting WGM resonances that are more tightly spaced than the resolution of the reader 14 utilized to measure the light exiting the resonator 18. This is achieved by using resonators generally larger than 50 µm in diameter.

Light from the light source 12 that is coupled into the resonator 18 propagates around the perimeter of the resonator 18 in WGM resonances by continuous internal reflection. As the light travels around the perimeter of the resonator 18, an evanescent field of photons of light extends slightly beyond the resonator 18. The evanescent field of photons interacts with a sample to be tested that preferably substantially envelops the resonator 18. The evanescent field of photons which extends slightly beyond the resonator 18 travels into the sample to be tested which is disposed in close proximity to the resonator 18. The photons of light within the evanescent field interact or react with the molecules of the sample many times as the light propagates around the perimeter of the resonator 18. In the resulting interaction or reaction between the evanescent field of photons and the sample, absorption may occur which is then measured by the reader 14.

The relationship between the concentration of an absorbing material in the sample and the absorbance measured by the reader 14 at a particular wavelength is given by Beer's Law:

$$A = -\log T = -\log(I \div I_o) = \epsilon bc$$

Where T is the transmittance through the sample and is equal to the ratio of the intensity of the light exiting the sample, I, and the intensity of the light entering the sample, $I_o$. The three quantities on the right side of Beer's law are the extinction coefficient of the absorbing material, $\epsilon$; the path length through the material, b; and the concentration of the absorbing material, c. For a given absorber species, $\epsilon$ is fixed. The minimum measurable absorbance value, A, is also fixed. The path length through the sample determines the minimum detection level.

Figure 2:
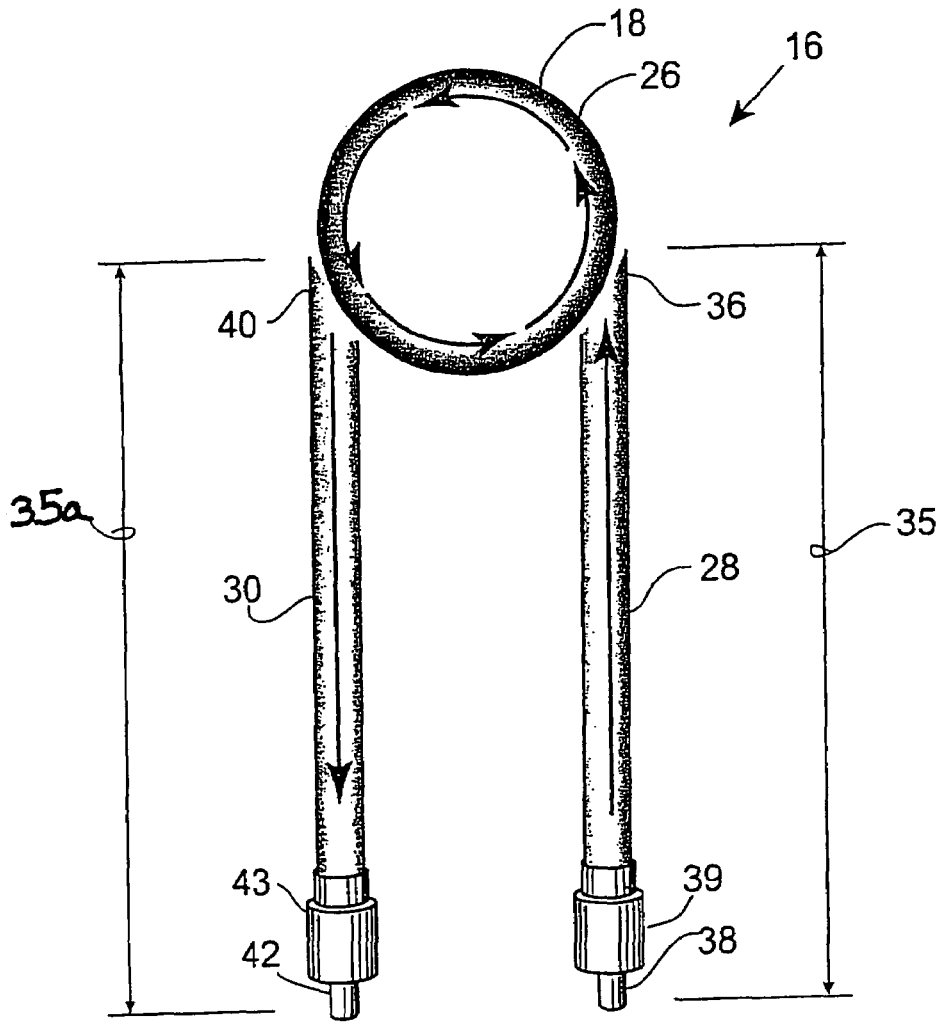
FIG. 2 is a side elevational view of probe for colorimetric testing.

Referring now to FIGS. 2, 2A and 2B, shown therein in more detail is the probe 16. In this embodiment of the probe 16, the resonator 18 is configured as a spheroid of optically transparent material 26, sometimes referred to as the sphere 26, the first coupler 20 is configured as a first optical fiber 28 and the second coupler 22 is configured as a second optical fiber 30.

The processes for fabricating spheroids of optically transparent material and optical fiber are well known in the industry and will not be discussed in detail herein. One advantage of constructing the first and second couplers 20 and 22 of optical fiber is that optical fiber can be economically terminated to provide low-cost connections that are compatible with available light sources and readers.

Another advantage of the system 10 over traditional systems for colorimetric testing is that the minimum sample needed to perform a colorimetric test utilizing the probe 16 is set by the amount of the sample required to envelop the evanescent field of the photons substantially surrounding the resonator 18. For example, if the resonator 18 is configured as a spheroid, 1 µL of a defined sample would cover the surface of a 1 mm diameter spheroid of optically transparent material to an approximate depth of 200 µm which is many times the evanescent field penetration.

In the present embodiment, the first optical fiber 28 has a length 35, a first end 36, and a second end 38. The first end 36 of the first optical fiber 28 is positioned adjacent the resonator 18. The second end 38 of the first optical fiber 28 is in communication with the light source 12. The probe 16 can also include a first connector 39 connected to the second end 38 of the first optical fiber 28 compatible with the light source 12 for connecting the first optical fiber 28 to the light source 12. The process for making and using connectors for optical fiber is well known in the industry and will not be discussed herein. The first end 36 is angled and polished so as to facilitate the transfer of light from the first optical fiber 28 to the resonator 18. The first end 36 of the first optical fiber 28 serves the role of a prism. When the first end 36 of the first optical fiber 28 is brought to the surface of the spheroid of optically transparent material 26, overlapping evanescent fields of the first end 36 of the first optical fiber 28 and of the spheroid of optically transparent material 26 form an evanescent tunnel where light can couple between the first optical fiber 28 and the spheroid of optically transparent material 26. The first end 36 and the second end 38 of the first optical fiber 28 are in communication with each other and the light source 12 and spheroid of optically transparent material 26 such that at least a portion of the light from the light source 12 is directed from the light source 12 to the second end 38 of the first optical fiber 28, through the length 35 of the first optical fiber 28, to the first end 36 and coupled from the first end 36 into the spheroid of optically transparent material 26.

The second optical fiber 30 has a length 35a, first end 40 and a second end 42. The first end 40 is positioned within the evanescent field produced by the spheroid of optically transparent material 26. The first end 40 of the second optical fiber 30 also acts as a prism. The second end 42 of the second optical fiber 30 is in communication with the reader 14. The probe 16 can also include a second connector 43 connected to the second end 42 of the second optical fiber 30 compatible with the reader 14 for connecting the second optical fiber 30 to the reader 14. The first end 36 of the second optical fiber 30 is coupled to the spheroid of optically transparent material 26 preferably opposite the side of the spheroid of optically transparent material 26 from where the first end 36 of the first optical fiber 28 was coupled to the spheroid of optically transparent material 26. When the first end 40 of the second optical fiber 30 is brought to the surface of the spheroid of optically transparent material 26, overlapping evanescent fields of the first end 40 of the second optical fiber 30 and the spheroid of optically transparent material 26 form an evanescent tunnel where the light can couple between the first end 40 of the second optical fiber 30 and the spheroid of optically transparent material 26. The first end 40 of the second optical fiber 30 and the second end 42 of the second optical fiber 30 are in communication with the spheroid of optically transparent material 26 and the reader 14 respectively such that at least a portion of light from the spheroid of optically transparent material 26 is coupled from the spheroid of optically transparent material 26 to the first end 36 of the second optical fiber 30, through the length 35a of the second optical fiber 30, to the second end 42 of the second optical fiber 30 and to the reader 14 allowing the light to be exploited for chemical analysis through absorption spectroscopy for instance. The appropriate angle to polish the first ends 36 and 40 of the first and second optical fiber 28 and 30 will be discussed in more detail later.

The system 10 will greatly improve the range of colorimetric testing through improved portability, enhanced cost-effectiveness, reduced consumption and waste of the sample, simplification of operation and better sensitivity in smaller sample volumes. These characteristics will make colorimetric testing practical in long term monitoring applications and for in process systems such as remediation and recovery operations.

An advantage of the probe 16 is that fluidic connections for the probe 16 can be made compatible with standard fittings (such as commercially available mixing T's) that are used in high performance chromatography, flow injection analysis and similar automated analysis systems.

Referring now to FIG. 3, shown therein is an inline sample cell 44. In this configuration the sample flows past the resonator 18 of the probe 16 in a standard T connection. The inline sample cell 44 includes the probe 16, a mixing T 46 having an input 47 for receiving an inflow line 48, an output 49 for receiving an outflow line 50, and a plurality of connectors 52 for connecting the probe 16, the inflow line 48, and the outflow line 50 to the mixing T 46. The probe 16, the inflow line 48 and outflow line 50 are connected to the mixing T 46 using the plurality of connectors 52, such that, in operation the sample to be tested flows from the inflow line 48 into the mixing T 46 and past the resonator 18 of the probe 16 in such a manner that the sample substantially envelops the evanescent field of photons surrounding the resonator 18, interacts or reacts with the evanescent field of photons and thereafter the sample discharges out of the output 49 of the mixing T 46 and to the outflow line 50. The interaction or reaction of the evanescent field of photons and the sample is analyzed by the reader 14 as previously described. Although the mixing T 46 is described and depicted as having a single input 47 connected to the inflow line 48 and a single output 49 connected to the outflow line 50, those skilled in the art will readily recognize and understand that any plurality of inputs and outputs could be connected to the inflow and outflow lines 48 and 50, respectively, and integrated into the mixing T 46, or a similar mixing apparatus of appropriate configuration taking into consideration the number of inflow and outflow lines 48 and 50. It will also be recognized and understood by those skilled in the art that a plurality of probes 16 could be included in the sample cell 44 for providing redundancy.

In order to calculate the correct angle to polish the first ends 36 and 40 of the first and second optical fibers 28 and 30; and in order to determine the WGM resonance frequencies of the spheroid of optically transparent material 26, a number of factors need to be taken into consideration, such as, the energy keeping or frequency selecting capability of the spheroid of optically transparent material 26, the quality factor of the spheroid of optically transparent material 26, the resonant electromagnetic field components inside the spheroid of optically transparent material 26, Free Spectral Range (FSR), which is the frequency spacing between adjacent major modes, and the effective refractive indices of the spheroid of optically transparent material 26, of the first and second optical fibers 28 and 30, and of the enveloping sample.

The energy keeping or frequency selecting capability of the spheroid of optically transparent material 26 is characterized by its Quality factor (Q). A high Q factor provides for a long effective path length. A long effective path length means that the light can make numerous trips around the spheroid of optically transparent material 26 so that the photons of light in the evanescent field can interact with the molecules of the substance to be tested a number of times.

The Q factor of the spheroid of optically transparent material 26 is determined by several loss factors such as radiation loss due to curvature, scattering loss because of inhomogeneity of the spheroid of optically transparent material 26, absorption by the spheroid of optically transparent material 26, and absorption by surface contamination or surrounding material. The unloaded Q factor (with no coupler present) is expressed by the unloaded Q factor equation:

$$Q^{-1} = Q_{rad}^{-1} + Q_{scat}^{-1} + Q_{mat}^{-1} + Q_{surf}^{-1}$$

Each of the terms on the right side of the above equation may be examined independently to determine its effect upon the total Q of the spheroid of optically transparent material 26.

Radiation loss reduces rapidly with increasing sphere size of the spheroid of optically transparent material 26. For diameters greater than $15\lambda$, $Q_{rad}$ is greater than $10^{11}$, where $\lambda$ is the vacuum wavelength of the entrapped light. The scattering Q factor has been generally reported in the literature as having a limit of $10^{10}$.

The material absorption presents a fixed limitation regardless of the size of the spheroid of optically transparent material 26. The material Q factor can be expressed as $$Q_{mat} = 2\pi n/\alpha\lambda,$$

where a is the loss per meter traveled. For example, the silica used in optical fiber has attenuation of about 7 dB/km at 633 nm (5-dB bulk Rayleigh scattering loss and 2-dB absorption), which translates to $a=1.588\times10^{-3}$ and a maximum total Q factor of about $0.9\times10^{10}$. Experimentally, the Q factor can be found by measuring the energy damping time $\tau=Q/(2\pi f)$. This examination indicates that measured Q's below $10^{10}$ can be attributed to coupling losses (not yet discussed) or absorption by surface contaminants or surrounding media.

Since the system 10 utilizes the evanescent field outside the spheroid of optically transparent material 26 to interact with the analyzed material and because the evanescent field contains only a portion of the total energy within the spheroid of optically transparent material 26 and its intensity drops exponentially, it is intuitive to assume the sensitivity will be less than that of direct absorption spectroscopy. However, the sensitivity of the system 10 can be optimized to be even greater than that of a traditional direct absorption spectroscopy system which utilizes an open path beam.

The energy distribution of a WGM mode can be described by the resonant electromagnetic field components inside the sphere of optically transparent material 26:

$$E_r = 0$$

$$E_\theta \propto j_l(kr) \frac{P_l^m(\cos\theta)}{\sin\theta} e^{im\phi} \text{ (TE mode)}$$

$$E_\phi \propto j_l(kr) \frac{\partial P_l^m(\cos\theta)}{\partial \theta} e^{im\phi}$$

where $j_l$ and $P_l^m$ are the spherical Bessel function and associated Legendre function, and k is the wave number inside the sphere. Outside the sphere of optically transparent material 26, the spherical Bessel function $j_l$ is replaced by the spherical Hankel function of the 1$^{st}$ kind $h_l^{(1)}$.

Figure 4:
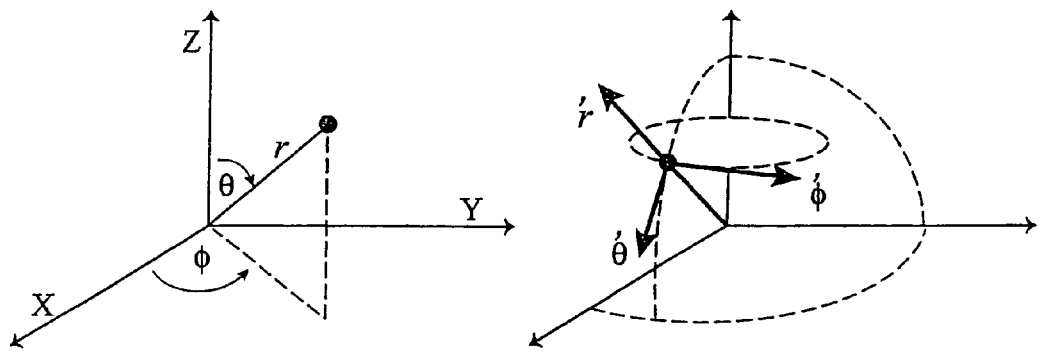
FIG. 4 shows an exemplary spherical coordinate system.

FIG. 4 illustrates the spherical coordinate system and orthogonal unit vectors. The potential function has a radial (r) dependence defined by the spherical Bessel function inside the spheroid of optically transparent material 26 and the spherical Hankel function of the 1$^{st}$ kind outside the spheroid of optically transparent material 26, a latitudinal angle dependence ($\theta$) is specified by the associated Legendre function, and azimuthal angle ($\phi$) dependence described by the complex exponential function.

The tangential components of the electric and magnetic fields need to be continuous across the surface of the spheroid of optically transparent material 26. Such boundary condition can be expressed by the characteristic equation.

$$\frac{[k_1 R j_l(k_1 R)]'}{j_l(k_1 R)} = \frac{[k_2 R h_l^{(1)}(k_2 R)]'}{h_l^{(1)}(k_2 R)},$$

where $$k_1 = \frac{2\pi n_1}{\lambda} \text{ and } k_2 = \frac{2\pi n_2}{\lambda}$$

are the wave number inside and outside the spheroid of optically transparent material 26, and the derivatives are with respect to $k_{1,2}R$, respectively.

By solving the boundary equation, the resonance frequency of the spheroid of optically transparent material 26 can be determined, with the resonance frequency depending on the mode number l. If l is sufficiently large, multiple solutions to the Boundary condition equation will exist. These are denoted by a secondary index, q. The root giving the lowest mode (i.e., lowest resonance frequency) is denoted by mode index q=1, with q=2, 3, . . . for the successively higher modes. A third index, m, is also needed to fully describe the structure of a WGM resonance.

Figure 5:
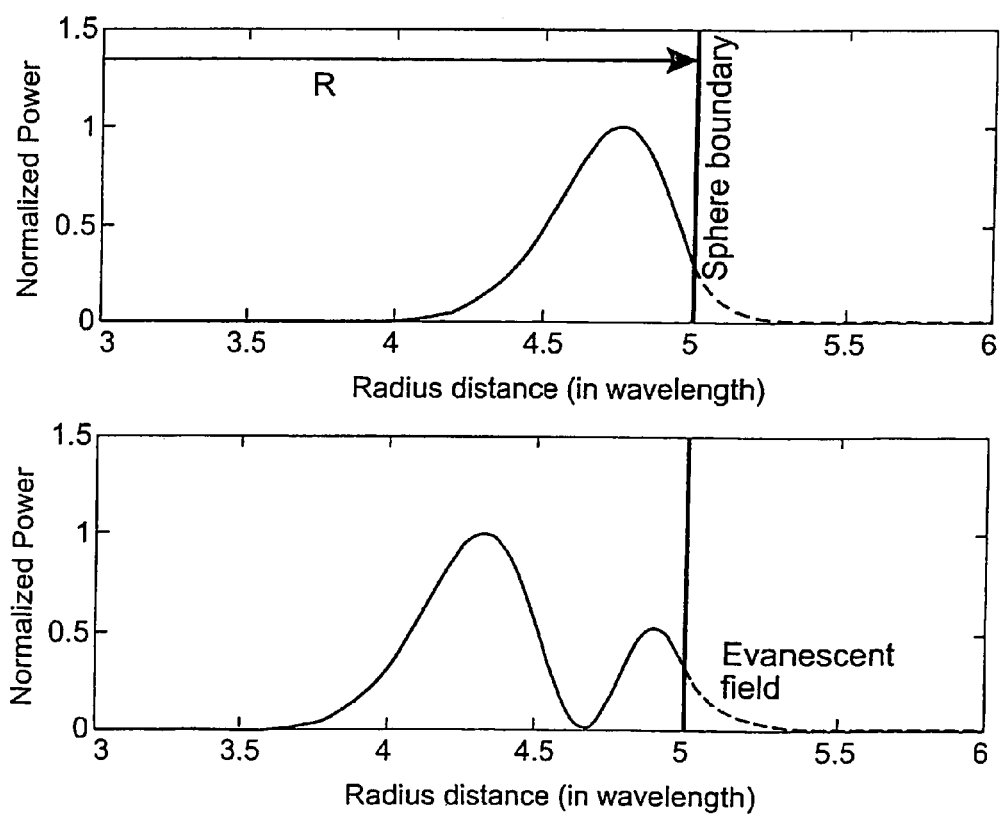
FIG. 5 shows the radial distance dependence of a Whispering Gallery Mode.

FIG. 5 illustrates the radial dependence of a WGM in the spheroid of optically transparent material 26 with radius of five wavelengths. The top figure is $TE_{l=50,m,q=1}$ mode, which has one major energy peak close to the surface. The bottom figure is $TE_{l=50,m,q=2}$ mode, showing that the first peak moves toward the center of the spheroid of optically transparent material 26 while the second peak maintains the evanescent field.

Figure 6:
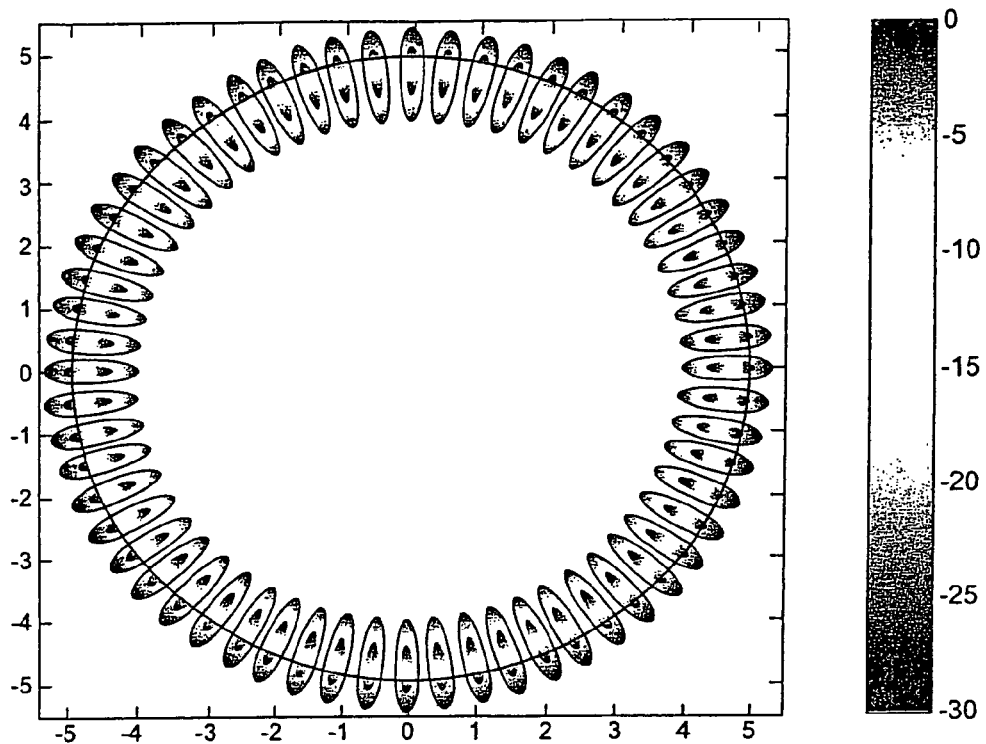
FIG. 6 shows the Whispering Gallery Mode field potential of a 5-µm spheroid of optically transparent material shown in decibels at the equatorial (x-y) plane.

The azimuthal angle dependence is specified by a traveling sinusoidal wave, which can be visualized as a simple $\cos(m\phi)$ distribution around the spheroid of optically transparent material 26. Referring to FIG. 6, the radial distance and azimuthal angle dependence are combined into a contour plot. This two-dimensional simulation of the WGM energy at the $\theta=90°$ equatorial plane (x-y plane) has been shown in dB. The spheroid of optically transparent material 26 boundary is marked by a circle. The evanescent field quickly drops down outside the boundary.

Figure 7:
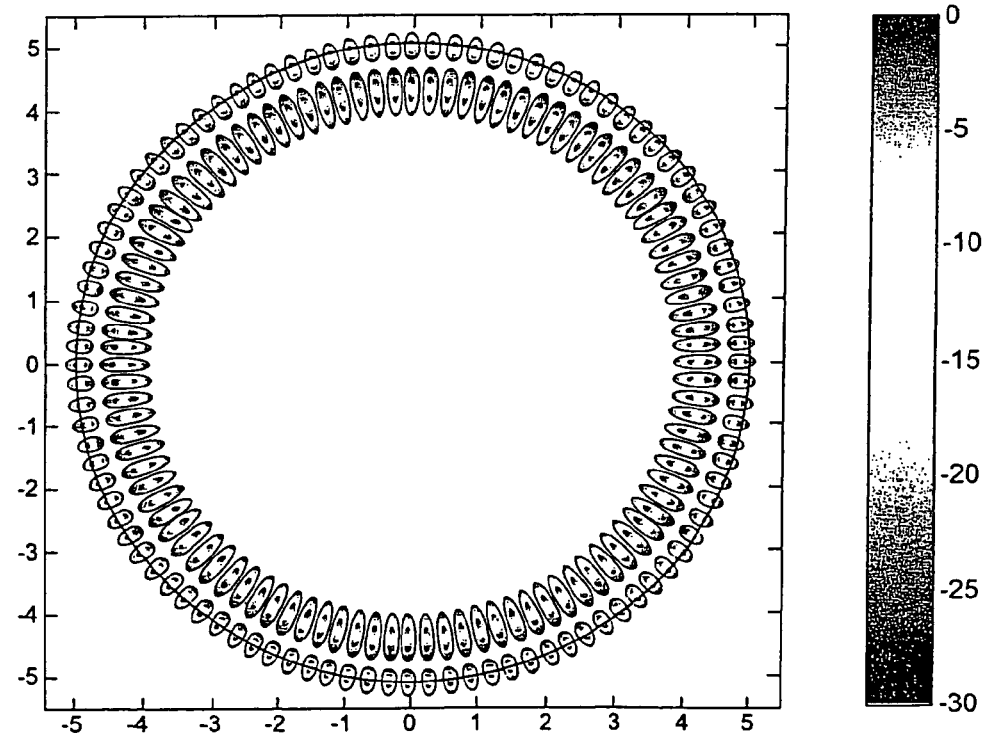
FIG. 7 shows Whispering Gallery Mode high radial mode with L=M=50, q=2.

Referring to FIG. 7 plotted therein is the higher radial mode with q=2 combined with azimuthal dependence (m=50). The major ring with higher energy goes toward the center of the spheroid of optically transparent material 26 with an additional weaker ring appearing beneath the surface. Such higher modes may not exist for smaller mode number l-the $R/\lambda$ ratio must exceed a threshold for the higher modes to be present.

When index m equals l, most of the energy concentrates at the equator. As mode index l differs from m, the WGM energy spreads symmetrically in the latitudinal directions, and the "ring" distribution becomes a wider "band" distribution.

Figure 8:
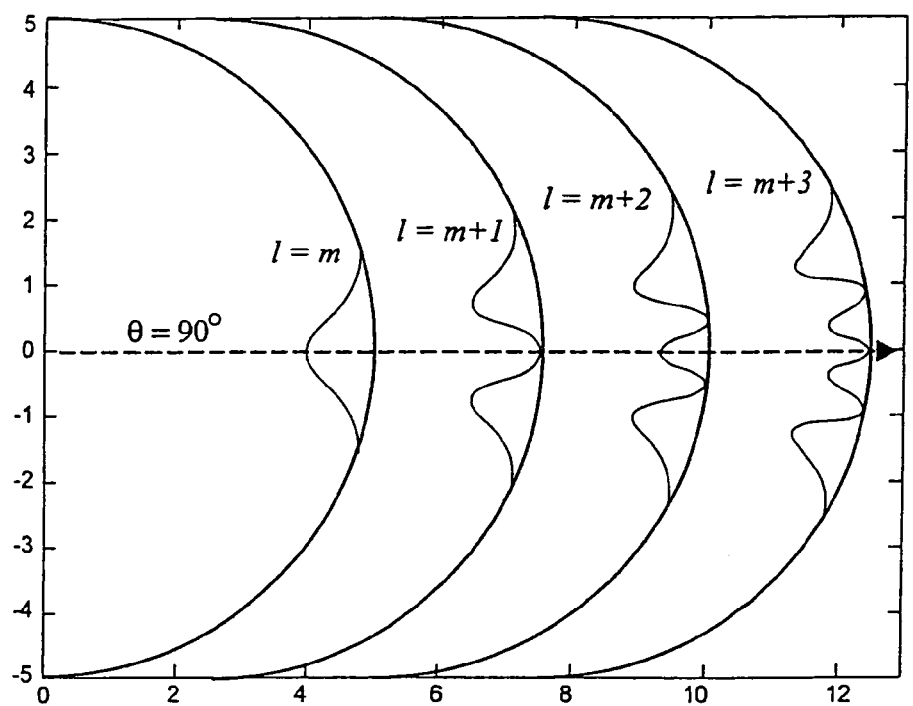
FIG. 8 shows a normalized power distribution of the Whispering Gallery Mode potential along the latitudinal angle.

FIG. 8 illustrates that (l−m+1) lobes exist, symmetrically-spaced with respect to the equator of the spheroid of optically transparent material 26. The maximum spread angle is $\cos(m/l)$.

Figure 9:
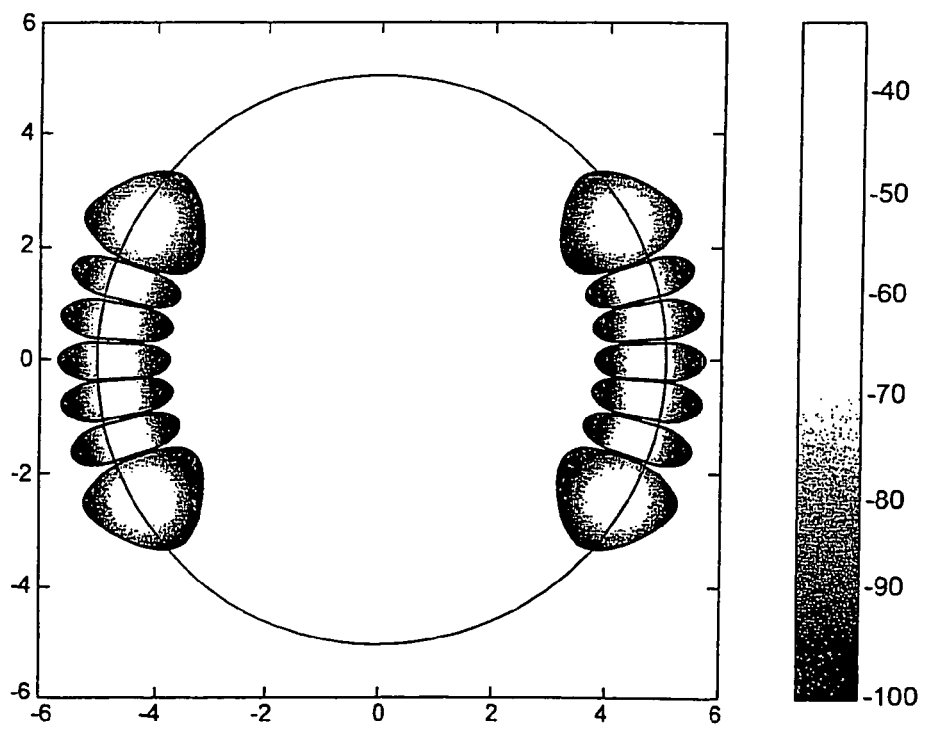
FIG. 9 shows a Whispering Gallery Mode field potential of a 5/µm spheroid of optically transparent material with a mode index L−M=6 shown in decibels at the vertical (x-z) plane.
Figure 16:
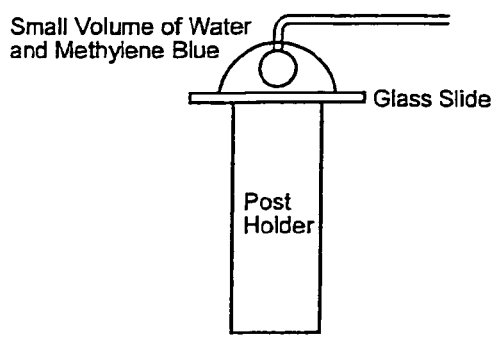
FIG. 16 shows the spheroid of optically transparent material in a liquid envelope.
Figure 17:
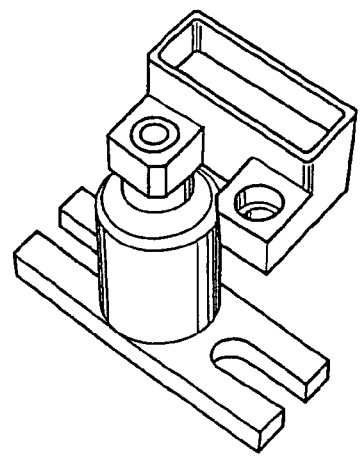
FIG. 17 shows a delrin trough.

The combination of radial distance and latitudinal angle dependence can also be visualized in a contour plot. A snapshot of the WGM potential with l−m=6 at $\phi=90°$ vertical plane (x-z plane) is shown in FIG. 9. There are l−m+1 lobes appearing symmetrically with respect to the equator of the spheroid of optically transparent material 26. If the coupling conditions are right, more than one mode with index l≠m may be excited inside the spheroid of optically transparent material 26.

The major WGM is the mode with l=m and q=1. Since the ray is propagating almost exactly on the equator of the spheroid of optically transparent material 26 and the propagation phase angle has to match around the circle, the mode number is l=m ≈$2\pi Rn/\lambda$ where R is the radius—so that the mode index m equals the number of wavelengths around the equator. This gives a simplified relation between the resonance frequency and mode number. The free spectral range (FSR), which is the frequency spacing between adjacent major modes (successive l), can then be estimated by $$FSR = \frac{c}{2\pi R n}$$

where c is the vacuum speed of light.

Referring now to FIG. 10, shown therein is a comparison of the WGM major mode resonance spacing in a 0.75 mm diameter spheroid of optically transparent material 26 and the dimensions of a typical visible absorbance spectrum. Although these major modes shift with temperature and pressure applied to the spheroid of optically transparent material 26, the result of such shifts is averaged out by the modest resolution of the analysis spectrometer and does not affect the resulting spectrum.

The resonance frequencies of a perfect spheroid of optically transparent material 26 are mainly decided by the mode numbers l—and q, if such modes exist. Modes with the same mode number l but different m—although separated spatially—will have the same resonance frequency. This is called mode degeneracy. However, the fabrication process will inevitably introduce a certain degree of eccentricity, $\epsilon$, to the spheroid of optically transparent material 26, splitting the degenerate modes.

The resonance frequency can be approximated by $$f_{qlm}^i \approx \frac{c}{2\pi R n}[l + 1/2 + a_q((l+1/2)/2)^{1/3} - \Delta^i];$$

when $$m = l,$$

where i denotes TE or TM, $a_q$ is the $q^{th}$ zero of the Airy function ($a_1$=2.338, $a_2$=4.088, $a_3$=5.521, etc.), R is the sphere radius, $$\Delta^{TE} = n/\sqrt{n^2-1}, \text{ and } \Delta^{TM} = [n\sqrt{n^2-1}]^{-1}.$$

and the frequency shifting due to eccentricity can be approximated by $$\frac{\Delta_f}{f} = \pm \frac{\varepsilon^2(l^2 - m^2)}{4l^2},$$

where the oblate spheroid of optically transparent material 26 has the positive sign and the stretched spheroid of optically transparent material 26 has the negative one. The spheroid of optically transparent material 26 then simultaneously supports multiple WGM resonances at closely-spaced frequencies around each major mode. With a coupling method that supports excitation of these modes, sufficient optical throughput is obtained for performing long path length spectroscopy using broadband illumination.

Electromagnetic energy can be transferred to or extracted from a spheroid of optically transparent material 26 through evanescent wave coupling with minimal impact upon the WGM resonance frequencies. Reflection from an internal prism face that is located near the surface of the spheroid of optically transparent material 26 overlaps the prism's and the spheroid of optically transparent material 26 evanescent fields and provides coupling, FIG. 11.

Although a prism coupler is flexible to use, it is also bulky and awkward because of its requirement for collimation optics and alignment. Angle-polished fibers provide a hybrid coupling method, which preserves the benefits of prism coupling while eliminating the collimating optics. Optical fiber conveniently delivers guided light to its angle-polished tip, which serves the role of a prism, FIG. 11.

When guided light strikes a spheroid of optically transparent material 26 optical fiber interface, as shown in FIG. 12a, at an angle greater than the critical angle, total internal reflection occurs, and an evanescent wave propagates parallel to the interface, FIG. 12b. The intensity of this evanescent wave decays exponentially with respect to the distance from the interface.

In order to support excitation of these modes and couple light from the light source 16 to the spheroid of optically transparent material 26 and from the spheroid of optically transparent material 26 to the reader 14, the first end 36 of the first optical fiber 28 and the first end 40 of the second optical fiber 30 must be polished to an angle and aligned at an angle with the spheroid of optically transparent material 26.

In order to polish and align the first and second optical fibers 28 and 30 correctly, the effective refractive indices of the spheroid of optically transparent material 26 and the first and second optical fiber 28 and 30 need to be found. The effective refractive index for the spheroid of optically transparent material 26 can be approximated by the equation:

$$n_{sphere} = \frac{l}{2\pi R/\lambda_0},$$

where $\lambda_0$ is the vacuum wavelength of the light to be coupled, l is the WGM mode number, and R is the radius of the spheroid of optically transparent material 26.

The effective refractive index for the first and second optical fibers 28 and 30 is non-trivial to find analytically, but may be approximated by the ratio of the fiber propagation constant ($\beta$) to the free-space propagation constant (k):

$$n_{fiber} = \frac{\beta}{k},$$

$$\text{where } k = \frac{2\pi}{\lambda}$$

The propagation constant of the fundamental $LP_{01}$ mode inside the first and second optical fibers 28 and 30 can be approximated by the equation $$\beta \approx kn_2\left[1 + \frac{n_1 - n_2}{n_1}\left(\frac{\alpha}{V}\right)^2\right],$$

where $n_1$ and $n_2$ are the refractive index of a fiber core of the first and second optical fibers 28 and 30 and cladding, respectively, a is the normalized transverse decay constant, and V is the normalized frequency.

After finding the effective refractive indices of the first and second optical fibers 28 and 30 and spheroid of optically transparent material 26, the fiber polishing and alignment angle is calculated by the equation $$\theta_c = \sin^{-1}\left(\frac{n_{sphere}}{n_{fiber}}\right)$$

where the $n_{sphere}$ and $n_{fiber}$ are the effective refractive indices for spheroid of optically transparent material 26 and the first and second optical fibers 28 and 30.

Two angle polished optical fibers can couple light into and out of the spheroid of optically transparent material 26 as shown in FIG. 13. With a single angle polished optical fiber coupling efficiencies of up to 60% have been demonstrated (~2.1-dB insertion loss). Maximum fiber to fiber transmission at resonance of about 23% has also been demonstrated in dual fiber arrangement.

Although the reported coupling efficiency obtained from angle-polished fibers (60%) is lower than prisms (80%) or tapered fibers (>90%), it is adequate and can be compensated for by employing a brighter light source 12. The important figure of merit for this system 10 is its long effective path length, not its coupling efficiency. So, angle-polished optical fibers, with their desirable mechanical advantages, are the preferred coupling method for this system 10.

As an alternative to first and second optical fibers 28 and 30 having angled polished first ends, the first and second optical fibers 28 and 30 can have first ends 36 and 40 tapered. In practice, a section of the first and second optical fibers 28 and 30 are heated and stretched to form a waist with a much smaller radius. The shape of the fiber radius reduction can be linear or curved. There are procedures to fabricate the tapered fiber with desired shape of tapering and excellent repeatability.

The key factor for efficient coupling using tapered fibers is to match the propagation constant of the light inside the spheroid of optically transparent material 26 and the first and second optical fibers. At the lowest mode of WGM resonance, the mode number 1 is approximately equal to the number of wavelengths around the spheroid of optically transparent material 26 waist. Therefore, the propagation constant of the spheroid resonance can be approximated by:

$$\beta_{sphere} \approx N_{sphere} k = \left(\frac{kl}{2\pi R/\lambda_0}\right) = \frac{L}{R}$$

where k and $\lambda_0$ are the free space propagation constant and wavelength, respectively.

For a fiber radius tapered down to a few micrometers, the propagation constant inside the taper can be expressed as $$\beta_{fiber} = k^2 n^2 - \left(\frac{2.405}{\rho}\right)^2,$$

where $\rho$ is the waist radius. By matching propagation constants, tapered fibers have reached 90–99.8% coupling efficiency, which is the highest of any coupling method.

A larger spheroid of optically transparent material 26 (>50μm in diameter) or one that supports high order WGM's due to eccentricity will provide tightly spaced resonances. Small rings provide more separated resonances, but are convenient for integrated planar applications.

The system 10 provides technical benefits such as long optical path lengths in microvolume liquids, convenient optical and fluidic interfaces, inexpensive illumination and detection requirements and a migration pathway to integrated lab-on-a-chip applications. Longer optical path lengths correspond to higher sensitivities. The system 10 enables long-path length absorbance spectroscopy in liquids at wavelengths from the ultraviolet to near infrared in microvolume samples. The system 10 permits long path length absorbance spectroscopy in 96- and 384-well plates, with extension to 1536-well plates possible. The system 10 could also be useful at a lab bench as a convenient method for examining single samples in microcentrifuge vials or test tubes.

Adoption of a component or technology is greatly aided by its compatibility with installed systems and expertise. Furthermore, fluidic connections for the system 10, always a problem with microfluidic components, will be compatible with standard ¼-28 fittings that are used in high performance liquid chromatography (HPLC), flow injection analysis (FIA), and similar automated analysis systems.

The system's 10 ability to transmit broadband light allows it to be used in moderate resolution absorbance spectroscopy. Light sources such as tungsten quartz halogen bulbs and spectrometers are readily available that permit the system 10 to be economical. For colorimetric applications where a single spectral band provides sufficient information, an LED source and Si detector could be utilized. Spheroids of optically transparent material 26 are only one type of resonator that could be used to enable long path length spectroscopy in liquids. Planar silicon-based micro-ring and micro-disk resonators could be designed into the channels of microfluidic systems and utilized for integrated optical measurements. Optical coupling to integrated waveguides could be accomplished using angle-polished optical fibers similar to those planned for use in the inline sample cell 44. The system 10 is also expected to provide environmental, health, and economic benefits, such as, reduced cost of sample analysis, improved drug discovery and expansion of point-of-care diagnosis.

By reducing the required reagents and generated waste, the system 10 will reduce the cost of performing lab-based liquid sample analyses using absorption spectroscopy. Such testing is widely used for environmental compliance and medical diagnosis. An expected effect of the system 10 would be the increased use of such testing as the per-test costs drop, perhaps catching diseases at an earlier stage where they can be more effectively treated.

Absorbance spectroscopy is difficult to implement in massively paralleled samples that are analyzed during drug discovery, due to the small sample sizes that reagent costs and waste disposal require. The system 10 allows absorbance spectroscopy to be widely applied to this area, reducing development costs.

When combined with lab-on-a-chip technology, an integrated resonator 18 will permit the transition of many lab-based analyses to the doctor's office. This will improve the level of care received by patients and enable more rapid diagnosis and treatment of ailments. This system 10 will be especially useful when hospital-based facilities are not readily available, such as in rural locations and military deployments.

Referring to FIG. 14, absorption measurements were initially performed using a HeNe laser (632 nm) and methylene blue dye with a spheroid of optically transparent material 26 and first and second optical fibers 28 and 30 have tapered first ends 36 and 40.

A 632 nm light from a 10 mW helium neon laser was focused by a microscope objective onto 200/225 multimode optical fiber. Fiber chucks held the first and second optical fibers 28 and 30 on Thorlabs XYZ translation stages. A 700 μm diameter spheroid of optically transparent material 26 was held by the spheroid's stem in a fiber chuck, which, in turn, was held by a 5-axis fiber positioner. The first and second optical fibers 28 and 30 were positioned on opposite sides of the spheroid of optically transparent material 26 as shown in FIG. 15. Light passing through the spheroid of optically transparent material 26 was detected with a fiber-coupled spectrometer, and data was collected and viewed on a computer. The first and second optical fibers 28 and 30 and spheroid of optically transparent material 26 were visually aligned with a microscope.

Initially the system 10 was aligned to obtain maximum through-coupling with the HeNe, then 15 μL of water were placed on the glass slide. The surface tension of the water disturbed the first and second optical fibers 28 and 30, so the first and second optical fibers of 28 and 30 and the spheroid of optically transparent material 26 were realigned in the drop. Next, 5.2 μL of 0.005% methylene blue was added to the drop, followed by 20 μL of water without further realignment.

Referring now to Table 1, when methylene blue was added to the drop, the through-coupling decreased. The measured effective path lengths, 9.1 cm and 13.6 cm, argue against reflection or lensing effects as valid explanations for the coupling between first and second optical fibers 28 and 30. When more water was added, the through-coupling actually increased as the concentration of methylene blue was lowered. The observation of decreased absorption with the addition of water to the water and methylene blue liquid envelope in both trials argued against misalignment of the first and second optical fibers 28 and 30 as an explanation of decreased throughput.

TABLE 1

Methylene blue absorption

|  | Trial 1 | Trial 2 |
| --- | --- | --- |
| Intensity with 15 μL water | 948 Arb. Units | 960 Arb. Units |
| Intensity with 5 μL blue | 643 Arb. Units | 537 Arb. Units |
| Intensity with 20 μL water | 799 Arb. Units | 653 Arb. Units |
| Percent of drop regained | 51.1% | 27.4% |
| Effective Path length | 9.1 cm | 13.6 cm |

To further validate WGM coupling as the cause of the long measured path lengths, the experiment was repeated using a tunable Ti:sapphire laser. Laser light was coupled into the WGMs of a fused-silica spheroid of optically transparent material 26 using a dual-tapered first optical fiber. A tapered second optical fiber, on the opposite side of the spheroid of optically transparent material 26, coupled light out of the WGMs. The power transmitted through the first and second optical fiber 28 and 30 was measured; the excitation of a WGM was identified by a dip in the power continuing down the first optical fiber 28 and by a peak in the power coming out of the second optical fiber 30. The spheroid of optically transparent material 26 and first and second optical fibers 28 and 30 tapers were then immersed in a weak solution of indocyanine green dye (ICG) in methanol.

Light of wavelength 790 nm, near the absorption peak of micromolar ICG in methanol, was produced by a cw Ti:sapphire laser pumped by a diode-pumped solid-state green laser. The laser light was focused with a high-quality short-focal-length lens into a single-mode optical fiber. A polarizer and quarter-wave plate before the lens reduced back-reflection into the laser from the injection face of the fiber. A fiber polarization controller before the coupling region then allowed conversion to linear polarization for selection of TE or TM WGMs. The first ends 36 and 40 of the first and second optical fiber 28 and 30 taper were produced by heating and stretching the first and second optical fibers 28 and 30 to produce regions, approximately 1 cm in length and 5 um in diameter, that could be brought into contact with the spheroid of optically transparent material 26 for coupling, with the optical fiber returning to normal size following the taper. Each coupling fiber was mounted on a holder so that the tapered section, bent into the shape of a flat-bottomed U, could be inserted into the sample solution while keeping the glue, which fastened the fiber to the holder, out of the solution. Three-axis positioning stages were used to carefully position the first and second optical fibers 28 and 30 in the proper positions and orientations next to the spheroid of optically transparent material 26. As the laser's frequency was tuned, detectors monitored the power on the first optical fiber 28 reflected from the spheroid of optically transparent material 26 and second optical fiber 30 transmitted through the spheroid of optically transparent material 26 via WGMs.

Positioning of the first and second optical fibers 28 and 30 was done by maximizing reflection dips and transmission peaks in air with the trough empty. When the WGM resonance signatures were clear, the trough was filled with a precisely measured volume of methanol and the first and second optical fibers 28 and 30 re-positioned, if necessary. Various concentrations of ICG were added by pipette, and changes in the dips and peaks observed simultaneously.

Reflection resonance dips in the reflected optical fiber output could be used to measure absorbance but were not used here primarily because these results could not be compared to similar results using a broadband source. With a broadband source, individual resonance dips are not resolved, which means that the reflected optical fiber output will consist of a very small change on a large background.

Two sequences of traces were identified using different modes. In both data sets, a sequence of scans over 1 GHz in frequency is presented, with the reliably identified mode at the center of the scan. By measuring the line width $\Delta v$ of the resonance peak, we can estimate the quality factor of the mode ($Q=v/\Delta v$). Using the pure methanol (zero concentration) trace, Q was estimated to be approximately $10^7$-in both trials. This relatively high value of the loaded Q (including the effect of coupling, which reduces the intrinsic value of Q) for a fiber-coupled microsphere is a result of the fact that the refractive index of methanol, nm=1.33, is fairly close to the index of the spheroid (n=1.45) and so has the effect of "smoothing out" the surface roughness and reducing scatter. This increases the intrinsic Q (without coupling, so not measured) of the modes. Immersing the spheroid of optically transparent material 26 in methanol also increases the evanescent volume fraction. It is the intrinsic Q, along with the evanescent volume fraction of a WGM, that determines absorbance sensitivity. The maximum transmitted power was approximately 1 μW.

Figure 18:
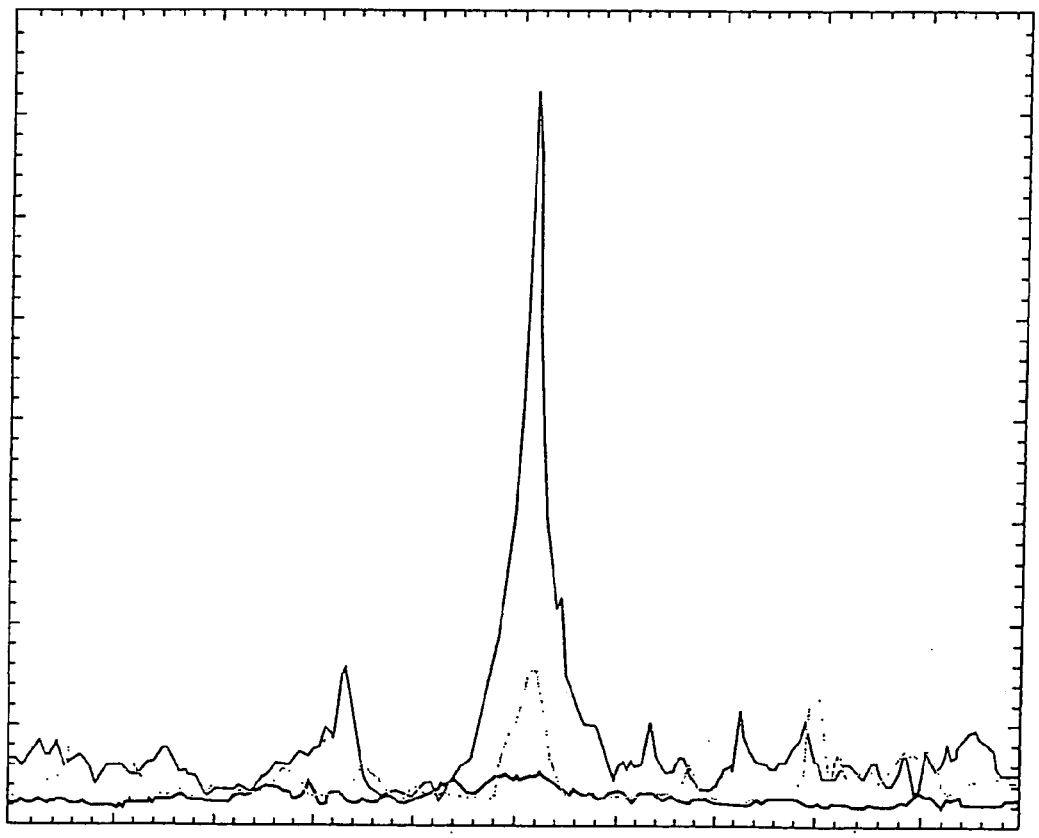
FIG. 18 shows 790 nm WGM transmission for three concentrations of Indocyanine green (ICG); spheroid of optically transparent material diameter equals 350 µm; scan range equals 1 GHz; wavelength equals 790 nm.

Referring now to FIG. 18, in the first data set, three traces at concentrations of 0, 0.476 μM, and 0.909 μM are shown. The broadening of the peak with increasing concentration, as absorption reduces the measured value of Q, should be noted.

Decreasing peak height corresponds to increasing concentration. Fitting these heights to an exponential, $T(a)=T(0)\exp(-a\ L_{eff})$, gives an effective absorption path length of $L_{eff}=8.8$ cm.

TABLE 2

Absorption data

| Concentration (μM) | Absorption (1/mm) | Transmission | Ln(T) |
| --- | --- | --- | --- |
| 0 | 0 | 7.1 | 1.960095 |
| 0.476 | 0.019 | 1.4 | 0.336472 |
| 0.909 | 0.036 | 0.3 | −1.20397 |

Figure 19:
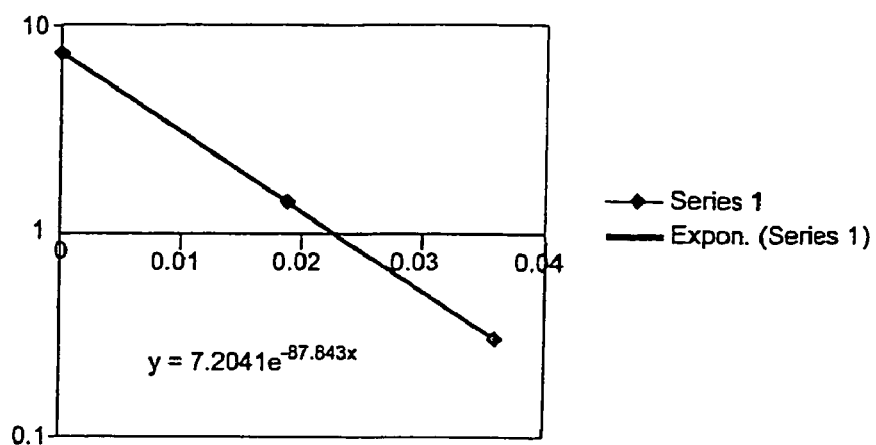
FIG. 19 shows Whispering Gallery Mode height versus ICG concentration.
Figure 20:
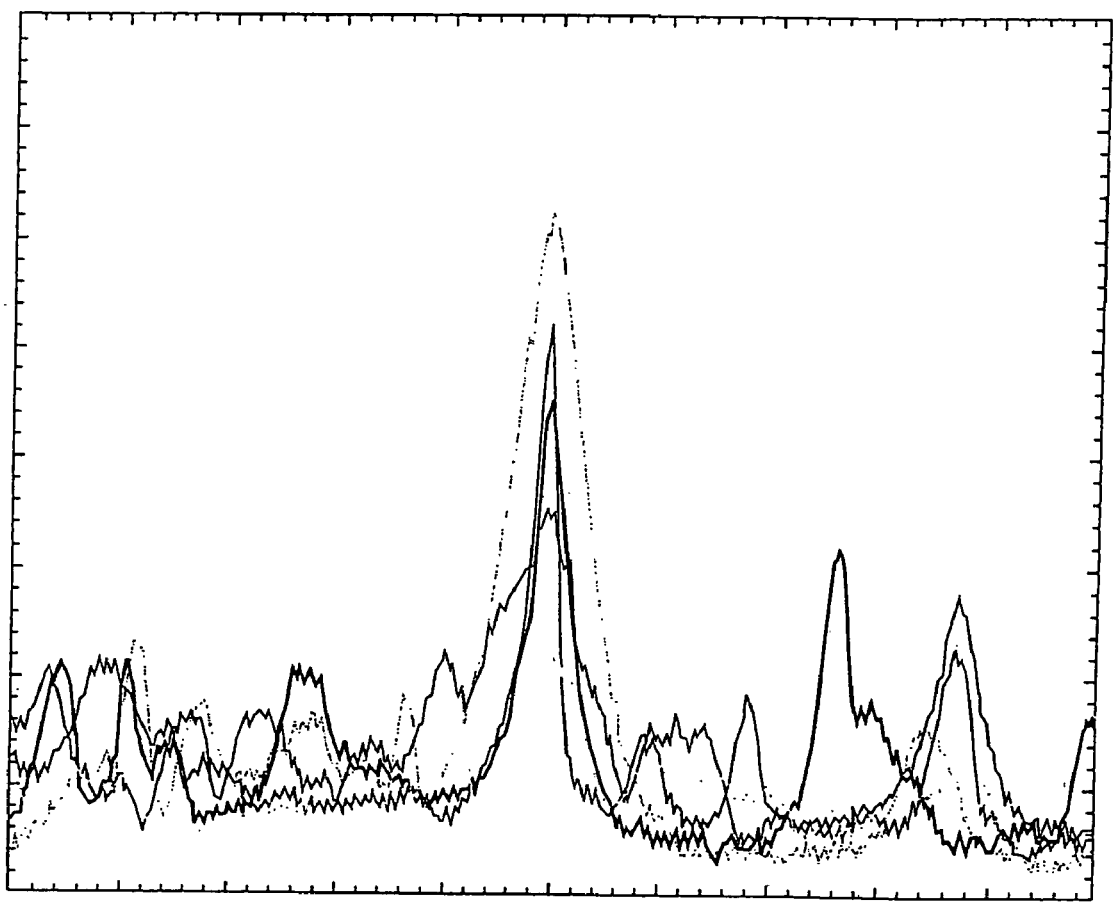
FIG. 20 depicts another 790 nm WGM transmission for three concentrations of ICG absorption; spheroid of optically transparent material diameter equals 350 µm; scan range equals 1 GHz; wavelength equals 790 nm.

Referring now to FIG. 19, the exponential fit to the data is very good. Referring now to FIG. 20, the second data set consists of five traces. The second-highest peak is for zero concentration and is not considered because a jump in the scan seems to have cut it off below its true height (note the asymmetry and narrow width of the peak). The trend in peak width is not consistent here, but the heights are not affected by the scan slowing that broadens the peak. Referring now to Table 3, the other four traces are for concentrations of 0.043 μM, 0.0826 μM, 0.118 μM, and 0.152 μM.

TABLE 3

Absorption Data

| | Trial 1 | Trial 2 | |
|---|---|---|---|
| Concentration (μM) | Absorption (1/mm) | Transmission | Ln (T) |
| 0.043 | 0.00172 | 6 | 1.791759 |
| 0.0826 | 0.003304 | 4.2 | 1.435085 |
| 0.118 | 0.00472 | 3.2 | 1.163151 |
| 0.152 | 0.00608 | 2 | 0.693147 |

Figure 21:
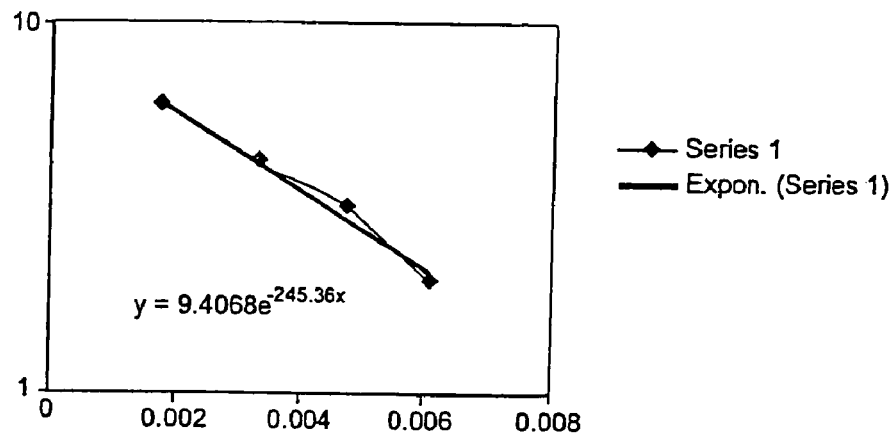
FIG. 21 depicts Whispering Gallery Mode height versus ICG concentration.

Referring now to FIG. 21, the transmission is fit reasonably well by an exponential, giving an effective absorption path length of $L_{eff}=25$ cm.

The circumference of the spheroid is 1.1 mm, and the evanescent volume fraction of a typical mode is probably on the order of f≅5%. With $L_{eff}=25$ cm, this means that the WGM intrinsic $Q=\pi n L_{eff}/\lambda f \cong 3\times 10^7$. The other observed value of $L_{eff}=8.8$ cm then implies an intrinsic $Q\cong 1\times 10^7$. Different WGMs will have different intrinsic Q values because of their different spatial field distributions. A range of a factor of three is well within normal expectations.

Figure 22:
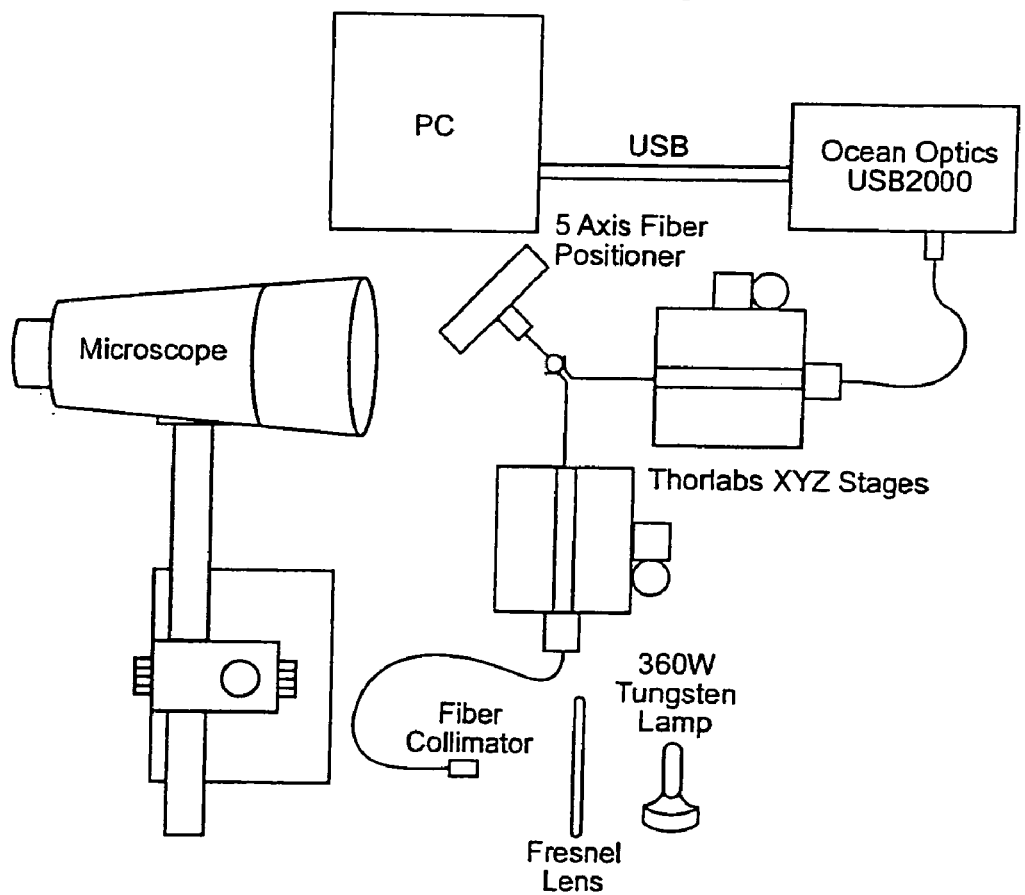
FIG. 22 shows arrangement of fiber coupled broadband absorption experiment.

Referring now to FIG. 22, in an experimental procedure, broadband light from a 360 W tungsten bulb was focused by a large fresnel lens and a fiber collimator into 200/225 multimode optical fiber. The first and second optical fibers were positioned on opposite sides of the spheroid of optically transparent material as in FIG. 15. Fiber chucks held the first and second optical single-tapered fibers on Thorlabs XYZ translation stages. The spheroid of optically transparent material was held by its stem in a fiber chuck, which in turn was held by a 5-axis fiber positioner. The spheroid of optically transparent material was approximately 750 μM in diameter.

The light that passed through the spheroid of optically transparent material and coupled into the second optical fiber was detected by a fiber-coupled spectrometer. The data was stored and viewed on a computer. The system was used to measure the absorption of crystal violet using the same methods as those previously discussed. Low concentrations of crystal violet were added to a freestanding volume of water surrounding the spheroid of optically transparent material. First, through-coupling was achieved with the broadband light source. 20 μL of water was added, and the coupling was realigned for the last time. Next, 5 μL of 1 ppm crystal violet was added to the water. The solution was then diluted by adding 20 μL of water to the drop. Lastly, 10 μL of 500 ppm crystal violet was added.

Figure 23:
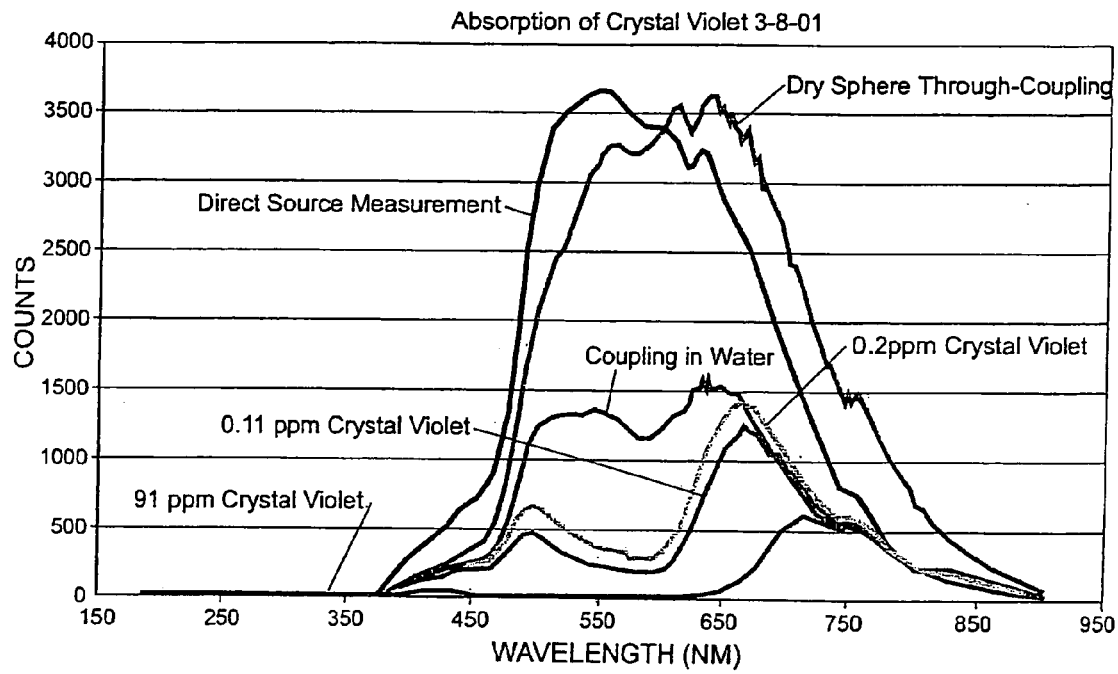
FIG. 23 shows broadband absorption of crystal violet.

Referring now to FIG. 23 shown therein in a representation, the spectra obtained during the experiment. These spectra are:

Direct Source Measurement: This data was taken by holding the spectrometer near the Light Source lamp. No optical fiber was used for collection. The amplitude is arbitrary.

Dry Sphere Through-Coupling: This data was taken through the tapered fibers and spheroid of optically transparent material 26 in air. Integration time: 1 sec. 207 pW was the maximum power coupled.

Coupling in Water: This data was taken after the spheroid of optically transparent material was submerged in 20 μL of deionized 18 megaohm-cm water. The coupling alignment was adjusted after the water was added. Integration time: 1 sec.; Coupled power: 3.

0.2 Crystal Violet: This data was taken about 30 sec after 5 μL of 1 ppm crystal violet solution was added to the 20 μL of water around the spheroid of optically transparent material.

Integration time: 1 sec.

0.11 Crystal Violet: This data was taken about 30 sec after 5 μL of water was added to the 0.2 ppm solution around the spheroid of optically transparent material 26. This data shows an increase in absorption instead of an expected decrease. It is suspected that that this was caused by poor mixing in the drop—water added to the edge of the drop pushed higher concentration crystal violet solution toward the spheroid of optically transparent material 26 as the added water took its place at the drop perimeter. Integration time: 1 sec.

91 ppm Crystal Violet: This data was taken after 10 μL of 500 ppm crystal violet was added to the drop. Integration time: 1 sec.

Using the absorbance of calibrated-concentration crystal violet solutions measured with a spectrophotometer at 591 nm, the 0.2 ppm measurement gives an effective absorption path length of 22.4 cm. The 0.11 ppm crystal violet measurement gives an effective absorption path length of 60.4 cm. The small changes in collected signal intensity at 750 nm and 450 nm indicate that only negligible misalignment could have occurred during the in-liquid measurements, changes in the coupling would have caused a wavelength-independent drop in transmission.

Figure 24:
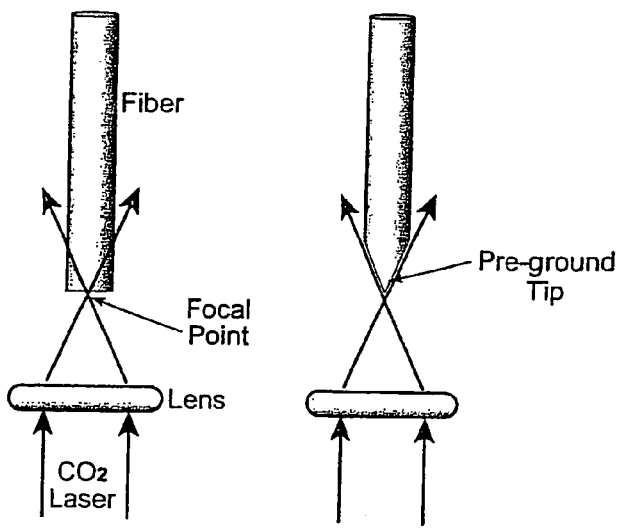
FIG. 24 shows microsphere fabrication method for (a) large sphere and (b) small sphere by $CO_2$ laser.

Spheroids of optically transparent material 26 have been fabricated from fused silica fiber using a hydrogen torch. Laser heating provides an alternative approach. Referring now to FIG. 24(a), in one such process, a $CO_2$ laser beam and silica fiber are aligned, the laser beam is projected paraxial with the silica fiber and focused into a small focal point. Due to the extremely small size of focal point (~60 μm in diameter) and the large vertical gradient of laser intensity, only a small amount of silica is fused. Spheroids as small as 60 μm in diameter can be fabricated by this method.

Referring now to FIG. 24(b), smaller spheroids of optically transparent material 26 can be made by a modified method. The tip of the optical fiber can be pre-ground into a cone shape to produce a spheroid of optically transparent material 26 approximately 40 μm in diameter. The precision control of the $CO_2$ laser power also avoids the possibility of overheating of the spheroid of optically transparent material 26, which may cause recrystallization of the silica.

Figure 25:
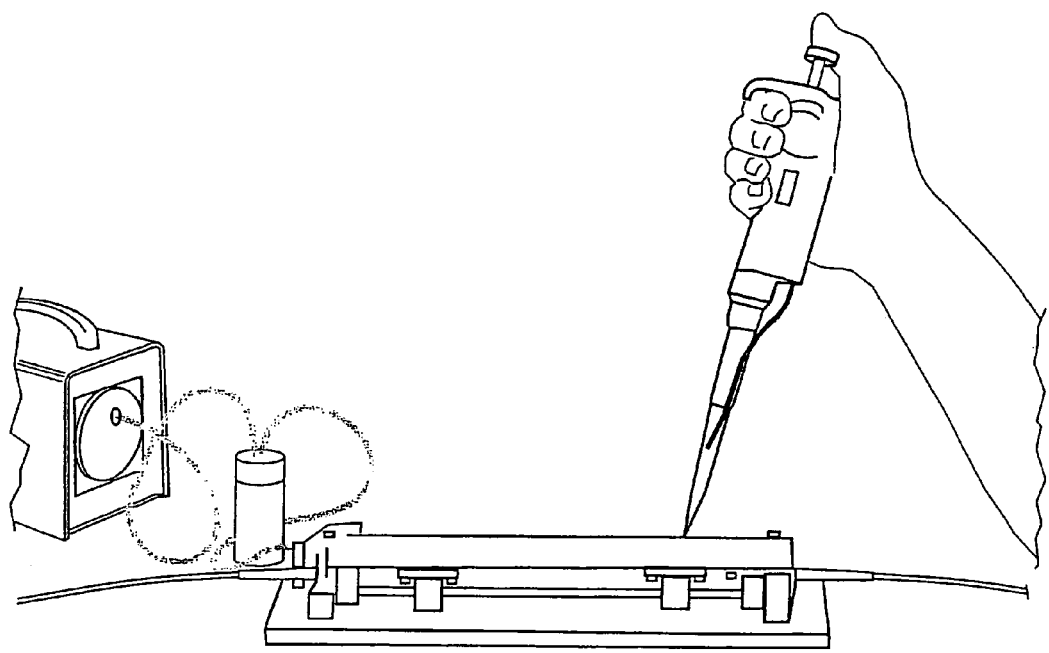
FIG. 25 shows commercially available 2.3 cm microvette, with attached vacuum pump to facilitate sample removable.

According to Beer's Law, the sensitivity of the absorption spectroscopy is proportional to the optical path length. Extending the path length with a given amount of sample has been an important goal for many researchers. Referring now to FIG. 25, the capillary micro-cuvette is an example of an existing approach. In this water-core waveguide based device, liquid samples are drawn into a rigid capillary to form the water-core waveguide. The input light propagates inside the capillary before being received by the reader 14. In order to prevent light escaping out of the water core, the material of the capillary is chosen so that the refractive index is lower than 1.33. In order to employ glass capillaries, a low refractive index polymer may be coated on the interior wall of the glass capillary. With the sample volume ranging from 4 to 15 microliters, the water core can be setup with a physical length between 2.3 cm and 10 cm.

Figure 26:
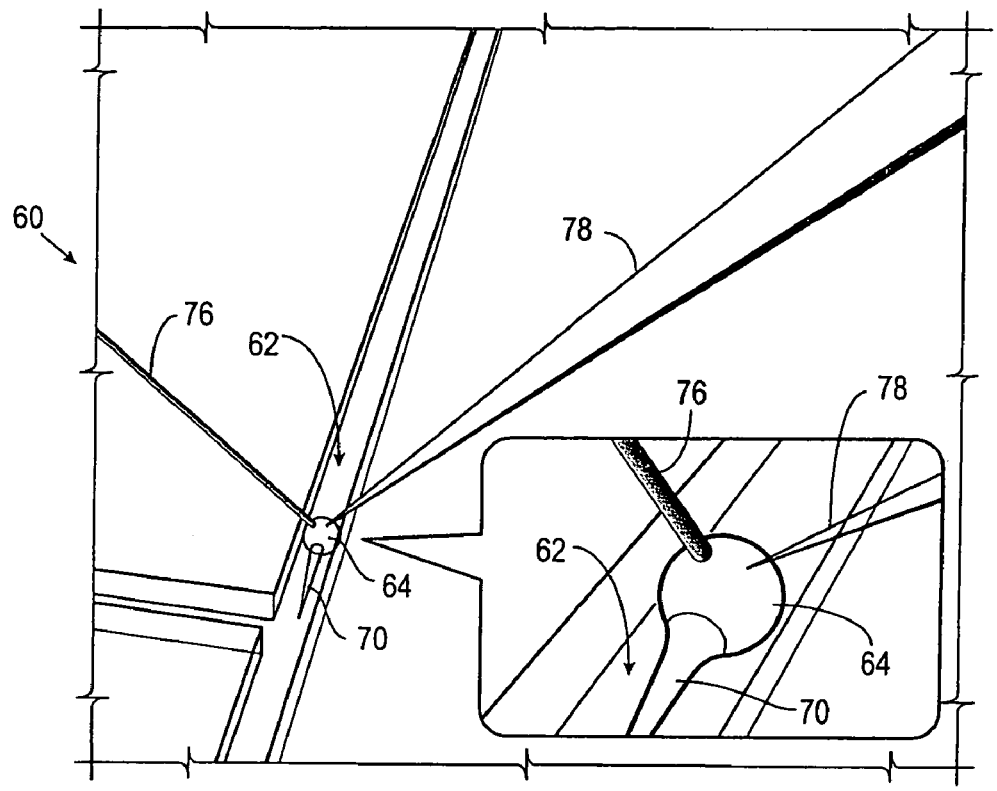
FIG. 26 is a perspective view of a microfluidic chip constructed in accordance with the present invention, a perspective inset view is shown of a microfluidic channel formed in the microfluidic chip.
Figure 27:
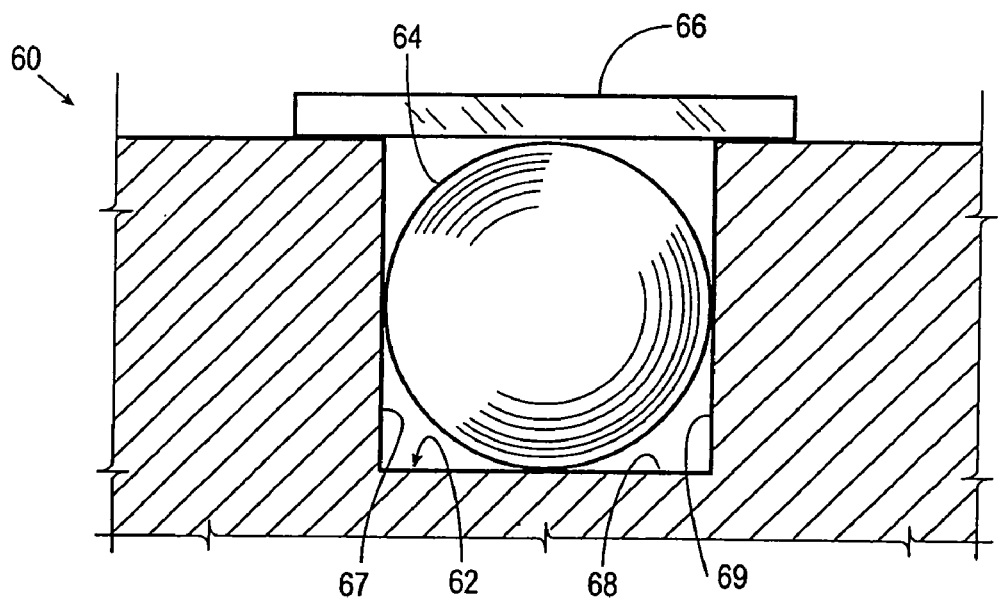
FIG. 27 is a cross-sectional view of a microresonator positioned within the microfluidic channel of the microfluidic chip of FIG. 26.

Referring to FIGS. 26–27, another embodiment of a system for colorimetric testing is shown utilizing a microfluidic chip 60. The microfluidic chip 60 is fabricated from a substrate of silicon, glass, or other material known in the art to construct the microfluidic chip, such as that used by Caliper Life Sciences. The microfluidic chip 60 is provided with at least one microfluidic channel 62, a microresonator 64, and at least one waveguide or surface 66. The microfluidic channel 62 includes three microchannel walls 67, 68, and 69 formed in the microfluidic chip 60. Preferably, the microfluidic channel 62 is formed by etching the microfluidic channel 62 into the substrate of the microfluidic chip 60 or into a layer of material which has been coated onto the substrate. The etching process produces the microfluidic channel walls that are needed to form the microfluidic channel 62. It is to be understood that the microfluidic channel 62 may be formed by any process known in the art. Further, the microfluidic channel 62 may be a microchannel flow cell.

A microresonator 64 is positioned within the microfluidic channel 62. The microresonator 64 may include a stem 70. The microresonator 64 is fixed within the microfluidic channel 62 either by its stem 70 or by trapping the microresonator 64 using structures within the microfluidic channel. The microresonator 64 is constructed of any of the following materials: silica, glass, quartz, silicon, GaAs, or materials containing gallium or silicon. The microresonator 64 can be constructed in various shapes, such as a sphere, spheroid, torus, disc, or cylinder.

At least one waveguide or surface is provided in the microfluidic chip 60. In one preferred embodiment, as shown in FIG. 27, a flat plate 66 is positioned over the formed microfluidic channel 62 to form a fourth wall of the microfluidic channel 62. (The flat plate 66 is removed from FIG. 26 for the purpose of more clearing showing the microfluidic channel 62.) The flat plate 66 is constructed of an optically transparent substrate. As shown in FIGS. 26 and 27, the flat plate 66 receives a light 76 having a frequency bandwidth greater than the spacing between the whispering gallery mode resonance frequencies. The light reaches the flat plate 66 via a prism (not shown) or other suitable optical coupler capable of producing an evanescent field at the inner surface of the flat plate 66. The flat plate 66 is evanescently coupled to the microresonator 64 such that supported whispering gallery mode resonance frequencies are coupled from the flat plate 66 into the microresonator 64 and light at frequencies not resonant with the microresonator 64 are not coupled into the microresonator 64. Further, light 78 is coupled out from the microresonator 64. Preferably, the optically transparent plate 66 is bonded to the substrate of the microfluidic channel 62. However, it should be understood that any other method or procedure known in the art for attaching the plate may be utilized for attaching the plate 74 to the substrate of the microfluidic chip 60. Alternatively, at least one other surface of the microfluidic channel 62 may be constructed so that the light reaches the other surface via the prism, grating, or other suitable optical coupler capable of producing an evanescent field at the other inner surface.

In another embodiment (not shown), at least one waveguide is embedded in the microfluidic channel 62 in proximity to the microresonator 64. The principal requirement for the preferred embodiments is that one of the surfaces that define the microfluidic channel 62 needs to support evanescent coupling to the microresonator 64. The microfluidic channel 62 may be fabricated within a single block, as long as the process employed is able to produce at least one channel wall that supports evanescent coupling to the microresonator 64.

In use of one preferred embodiment, a fluid (not shown) is transitioned into the microfluidic channel 62 of the microfluidic chip 60. Light 76 from a light source (not shown) is coupled through the flat plate 66 by use of the external prism. The light source is a light emitting diode, blackbody light source, an arc discharge light source, or a laser. The light 76 strikes an inner surface of the plate 66, where it is evanescently coupled into the microresonator 64. Light coupled into the microresonator 64 undergoes precession, so that upon coupling back out of the microresonator 64, it exits at a slightly different angle. The precession-based spatial separation of reflected and through-coupled beams allows the absorbance spectrum of the fluid in the microfluidic channel 62 to be measured.

Coupling into the microresonator 64 placed within a microfluidic channel 62 lends itself to parallelization to increase sample analysis throughput. Multiple microfluidic channels may be constructed and monitored by placing a microresonator 64 in each of the channels that need to be monitored. Light 76 is then coupled into each of the microresonators 64 using the same methods described above.

Changes may be made in the construction and the operation of the various components, elements and assemblies described herein or in the steps or the sequence of steps of the methods described herein without departing from the spirit and scope of the invention as defined in the following claims.

What is claimed:

1. A method for measuring the optical absorbance of a sample medium comprising:
   providing a light source emitting a light beam having a multitude of optical frequencies;
   providing a microfluidic chip comprising:
      a substrate defining a microfluidic channel;
      a microresonator being positioned within the microfluidic channel; and
      at least one waveguide receiving light having a frequency bandwidth greater than the spacing between the whispering gallery mode resonance frequencies, the at least one waveguide evanescently coupled to the microresonator such that supported whispering gallery mode resonance frequencies are coupled from the at least one waveguide into the microresonator and light at frequencies not resonant with the microresonator not coupling into the microresonator;
   disposing a sample medium into the microfluidic channel such that the sample medium substantially envelopes the microresonator;
   providing a reader for measuring at least a portion of the whispering gallery mode resonances coupled out of the microresonator;
   coupling the light beam into the at least one waveguide; and
   measuring the portion of the whispering gallery mode resonances coupled from the microresonator to the reader.

2. The method of claim 1 wherein the light source is a light emitting diode.

3. The method of claim 1 wherein the light source is a blackbody light source.

4. The method of claim 1 wherein the light source is an arc discharge light source.

5. The method of claim 1 wherein the reader incorporates an Si detector.

6. The method of claim 1 wherein the reader incorporates a spectrometer.

7. The method of claim 1 wherein the at least one waveguide is embedded in the microfluidic channel in proximity to the microresonator.

8. The method of claim 1 wherein the microfluidic channel is a microchannel flow cell.

9. The method of claim 1 wherein the microresonator is a sphere.

10. The method of claim 1 wherein the microresonator is a spheroid.

11. The method of claim 1 wherein the microresonator is a torus.

12. The method of claim 1 wherein the microresonator is a disc.

13. The method of claim 1 wherein the microresonator is a cylinder.

14. The method of claim 1 wherein the microresonator is made of the material selected from a group of materials consisting of silica, glass, quartz, silicon, GaAs, or materials containing gallium or silicon.

15. A method for measuring the optical absorbance of a sample medium comprising:
providing a light source emitting a light beam having a multitude of optical frequencies;
providing a microfluidic chip comprising:
a substrate defining a microfluidic channel;
a microresonator being positioned within the microfluidic channel; and
at least one surface receiving light having a frequency bandwidth greater than the spacing between the whispering gallery mode resonance frequencies, the at least one surface evanescently coupled to the microresonator such that supported whispering gallery mode resonance frequencies are coupled from the at least one surface into the microresonator and light at frequencies not resonant with the microresonator not coupling into the microresonator;
disposing a sample medium into the microfluidic channel such that the sample medium substantially envelopes the microresonator;
providing a reader for measuring at least a portion of the whispering gallery mode resonances coupled out of the microresonator;
coupling the light beam through the at least one surface; and
measuring the portion of the whispering gallery mode resonances coupled from the microresonator to the reader.

16. The method of claim 15 wherein the light source is a light emitting diode.

17. The method of claim 15 wherein the light source is a blackbody light source.

18. The method of claim 15 wherein the light source is an arc discharge light source.

19. The method of claim 15 wherein the reader incorporates an Si detector.

20. The method of claim 15 wherein the reader incorporates a spectrometer.

21. The method of claim 15 wherein the light reaches the at least one surface via a prism.

22. The method of claim 15 wherein the light reaches the at least one surface via a grating.

23. The method of claim 15 wherein the microfluidic channel is a microchannel flow cell.

24. The method of claim 15 wherein the microresonator is a sphere.

25. The method of claim 15 wherein the microresonator is a spheroid.

26. The method of claim 15 wherein the microresonator is a torus.

27. The method of claim 15 wherein the microresonator is a disc.

28. The method of claim 15 wherein the microresonator is a cylinder.

29. The method of claim 15 wherein the microresonator is made of the material selected from a group of materials consisting of silica, glass, quartz, silicon, GaAs, or materials containing gallium or silicon.

* * * * *